(12) United States Patent
Muraro et al.

(10) Patent No.: US 9,346,889 B2
(45) Date of Patent: May 24, 2016

(54) ERBB3 BINDING ANTIBODY

(75) Inventors: Raffaella Muraro, Bracciano (IT); Stefano Iacobelli, Rome (IT); Nicola Tinari, Montesilvano (IT); Sara Traini, Castel di Lama (IT); Gianluca Sala, Pescara (IT)

(73) Assignee: MEDIAPHARMA S.R.L., Chieti (IT)

( * ) Notice: Subject to any disclaimer, the term of this patent is extended or adjusted under 35 U.S.C. 154(b) by 89 days.

(21) Appl. No.: 13/880,114

(22) PCT Filed: Sep. 12, 2011

(86) PCT No.: PCT/EP2011/065771
§ 371 (c)(1),
(2), (4) Date: Apr. 18, 2013

(87) PCT Pub. No.: WO2012/052230
PCT Pub. Date: Apr. 26, 2012

(65) Prior Publication Data
US 2013/0224220 A1    Aug. 29, 2013

Related U.S. Application Data

(60) Provisional application No. 61/394,103, filed on Oct. 18, 2010.

(51) Int. Cl.
| | |
|---|---|
| *C12N 5/10* | (2006.01) |
| *C12N 15/10* | (2006.01) |
| *C12N 15/11* | (2006.01) |
| *C07K 16/28* | (2006.01) |
| *A61K 39/395* | (2006.01) |
| *C07K 16/40* | (2006.01) |
| *C07K 16/32* | (2006.01) |
| *A61K 45/06* | (2006.01) |
| *A61K 39/00* | (2006.01) |

(52) U.S. Cl.
CPC ........... *C07K 16/40* (2013.01); *A61K 39/39558* (2013.01); *A61K 45/06* (2013.01); *C07K 16/32* (2013.01); *A61K 2039/505* (2013.01); *C07K 2317/24* (2013.01); *C07K 2317/73* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 7,435,804 B2 * | 10/2008 | Kordyum et al. | |
| 7,867,493 B2 * | 1/2011 | Damiano et al. | |
| 7,977,461 B2 * | 7/2011 | Takayama et al. | |
| 8,168,427 B2 * | 5/2012 | Sahin et al. | |
| 8,394,938 B2 * | 3/2013 | Santner et al. | |

FOREIGN PATENT DOCUMENTS

| | | |
|---|---|---|
| WO | 2007077028 A2 | 7/2007 |
| WO | 2008100624 A2 | 8/2008 |

OTHER PUBLICATIONS

Chen et al., Enhancement and destruction of antibody function by somatic mutation: Unequal occurrence is controlled by V gene combinatorial associations, EMBO J., 14 (12): 2784-2794, 1995.*

(Continued)

*Primary Examiner* — Claire Kaufman
(74) *Attorney, Agent, or Firm* — Rothwell, Figg, Ernst & Manbeck, p.c.

(57) ABSTRACT

The present invention relates to an antibody, particularly a monoclonal antibody, which binds to the ErbB3 receptor, compositions comprising such an antibody as well as methods using such an antibody.

34 Claims, 21 Drawing Sheets

(56) References Cited

OTHER PUBLICATIONS

Lamminnaki et al., Crystal structure of a recombinant anti-estradiol Fab fragment in complex with 17Beta-estradiol, J. Biol. Chem. 276(39):36687-36694, Sep. 28, 2001.*

Jaiswal et al., Oncogenic ERBB3 mutations in human cancers. Cancer Cell, 23(5):603-617, May 13, 2013.*

Sithanandam et al., The ErbB3 receptor in cancer and cancer gene therapy, Canc. Gene Ther. 15(7):413-448, Jul. 2008.*

* cited by examiner

ERBB3 BINDING ANTIBODY

CROSS REFERENCE TO RELATED APPLICATION

This application is a 35 U.S.C. 371 National Phase Entry Application from PCT/EP2011/065771, filed Sep. 12, 2011, which claims the benefit of Provisional Application No. 61/394,103 filed on Oct. 18, 2010, the disclosure of which is incorporated herein in its entirety by reference.

The present invention relates to an antibody, particularly a monoclonal antibody, which binds to the ErbB3 receptor, wherein said binding reduces ErbB3 receptor mediated signal transduction, and compositions comprising such an antibody as well as methods using such an antibody.

Cancer is a disease characterized by uncontrolled proliferation of transformed cells that invade and destroy adjacent tissues, and may spread to distant anatomic sites through a process called metastasis[1-4]. In presence of metastatic disease, cancer may cause death in a variable period of time between a few months and some years[1-4].

The most used drugs for cancer treatment are cytotoxic chemotherapeutic agents (also called antiblastic agents or chemotherapeutic agents). These drugs act by damaging DNA or inhibiting cell proliferation. In this way, they kill all rapidly dividing cells, not only cancer cells, but also normal cells that are undergoing cell division. The lack of specificity of action of chemotherapeutic drugs on cancer cells is responsible for considerable toxicity following their administration. In the last decade, basic scientific research has significantly increased our knowledge about molecular mechanisms of cellular transformation and cell proliferation, leading to the development of "molecularly targeted" drugs or "targeted therapies"[5]. They refer to drugs that are specifically designed to act on cancer cells bearing particular molecular and/or functional abnormalities. However, also targeted therapies are associated with side effects, and in most cases they can block tumor growth only temporarily.

ErbB3 receptor, also known as HER-3, belongs to the epidermal growth factor receptor tyrosine kinase family (ErbB). This family of receptors consists of four members: ErbB1 (HER1), ErbB2 (HER2), ErbB3 (HER3) and ErbB4 (HER4). Many studies have suggested a critical role for ErbB receptors in cell survival, proliferation and differentiation, as well as in malignant transformation[6-7]. The signal transduction mediated by tyrosine kinase receptors is complex and involves the interaction with two categories of ligands: epidermal growth factor (EGF) and EGF-like ligands (e.g. TGFα and amphiregulin), Neuregulin (NRG), also defined Heregulin (HRG) or Neu Differentiation Factor (NDF). Ligand binding to ErbB receptors induces the formation of receptor homo- and heterodimers and activation of the intrinsic kinase domain, resulting in phosphorylation on specific tyrosine residues within the cytoplasmic tail. These phosphorylated residues serve as docking sites for a range of proteins, the recruitment of which leads to the activation of intracellular signalling pathways. Generally, heterodimerization is preferred over homodimerization; ErbB2 is the preferred heterodimerization partner of the other ErbB receptors, including ErbB1 (activated by EGF or EGF-like ligands), and ErbB3 and ErbB4 (activated by neuregulin, NRG). The two major signaling pathways activated by ErbB receptors are Ras-Raf-MAPK and PI3K-AKT pathways.[8-10]

ErbB2 gene is amplified in 20 to 30% of breast cancers and is correlated with a poor prognosis. In the same way, ErbB3 receptor has also been shown to be overexpressed in breast cancer patients. High levels of expression of both ErbB2 and ErbB3 receptors are associated with an aggressive biology of tumor. In fact, upon NRG stimulation, ErbB2/ErbB3 heterodimers deliver the most potent and long-lasting proliferative intracellular signal among the possible combinations of pairs of ErbB family members[8-11]. Several studies have suggested an important role of ErbB3 receptor in progression of many human tumor types, such as prostate cancer, melanoma, and gastric carcinoma.

All together, experimental and clinical data indicate that ErbB3 plays an essential role in tumor development and progression, suggesting that agents targeting ErbB3 could provide a novel and promising approach toward the treatment of some cancers.[12-24]

In spite of scientific progress and introduction into clinical practice of new chemotherapeutic agents and targeted therapies, cancer remains a disease difficult to cure, responsible for about 13% of deaths worldwide.[1-4]

Consequently, there is an urgent need to develop new antitumor therapies, more effective and possibly less toxic.

The inventor has found that specific ErbB3 inhibitors are able to induce tumor regression. In particular, the monoclonal antibody, MP-RM-1, has been used as an anti-ErbB3 inhibitor.

Thus, a first aspect of the present invention relates to an antibody or fragment thereof which binds to the ErbB3 receptor and which comprises
  a) a heavy chain amino acid sequence as encoded by SEQ ID NO: 1 or at least the variable domain thereof or an amino acid sequence having a sequence identity of at least 80% thereto and/or
  b) a light chain amino acid sequence as encoded by SEQ ID NO: 2 or at least the variable domain thereof or an amino acid sequence having a sequence identity of at least 80% thereto.

VH sequence
(SEQ ID NO: 1)
```
gacgtgcagctggtggagtctggggagacttagtgaagcctggagggtc cctgaaactctcctgtgtagtctctggattcactttcagtacctatgca tgtcttgggttcgccagactccagacaggaggctggagtgggtcgcaacc attagtcatggtgacggttataccactatccagacagtgtgaagggggcg attcaccatctccagagacaatgccaagaacaccctgcacctgcaaatga gcagtctgaagtctgaggacacagccatgtattactgtgcaagacatggg gattacgacgatgattactatgctatggactactggggtcaaggaacctc agtcaccgtctca
```

VL sequence
(SEQ ID NO: 2)
```
gatattgtgatgacccagtctccatcctccctgactgtgatagcaggaga gaaggtcactatgagctgcaagtccagtcagagtctgttaaacagtggaa atcaaaagaactacttgacctggtaccaacagaaaccagggcagcctcct aaactgttgatctactgggcatccactagggaatctggggtccctgatcg cttcacaggcagtggatctggaacagatttcactctcaccatcagcagtg tgcaggctgaagacctggcagtttattactgtcagaatgaatatacttat ccgctcacgttcggtgctgggaccaagctggagctgaaacggg
```

The term "antibody" as used herein includes "fragments" or "derivatives", which have at least one antigen binding site of the antibody and/or show the same biological activity.

Further, the antibody preferably comprises at least one heavy immunoglobulin chain and at least one light immunoglobulin chain. An immunoglobulin chain comprises a variable domain and optionally a constant domain. A variable domain may comprise complementary determining regions (CDRs), e.g. a CDR1, CDR2 and/or CDR3 region, and framework regions.

As used herein, "sequence identity" between two polypeptide sequences, indicates the percentage of amino acids that are identical between the sequences, preferably over the entire length of the amino acid sequences as encoded by SEQ ID NO: 1 and/or SEQ ID NO: 2. Preferred polypeptide sequences of the invention have a sequence identity of at least 80%, more preferably 85%, even more preferably 90%, 93%, 95%, 96%, 97%, 98% or 99%.

According to another preferred embodiment, antibodies of the invention reduce ErbB3 receptor mediated signal transduction. Said reduction of ErbB3 receptor mediated signal transduction is preferably caused by a down-regulation of ErbB3. According to a further embodiment, down-regulation of ErbB3 is preferably achieved by decreasing levels of ErbB3 on the cell surface, i.e. preferably the antibody of the invention has the ability to decrease levels of ErbB3 on cell surfaces.

The antibody of the invention may have at least one antigen binding site, e.g. one or two antigen binding sites.

The antibodies of the invention bind preferably to the extracellular domain of ErbB3.

The antibody may be any antibody of natural and/or synthetic origin, e.g. an antibody of mammalian origin. Preferably, the constant domain—if present—is a human constant domain. The variable domain is preferably a mammalian variable domain, e.g. a humanized or a human variable domain.

Antibodies according to the invention may be polyclonal or monoclonal antibodies. Monoclonal antibodies are preferred. In particular antibodies of the present invention are preferably selected from the group consisting of recombinant antibodies, humanized or fully human antibodies, chimeric antibodies, multispecific antibodies, in particular bispecific antibodies, or fragments thereof.

Monoclonal antibodies may be produced by any suitable method such as that of Köhler and Milstein [25] or by recombinant DNA methods. Monoclonal antibodies may also be isolated from phage antibody libraries using techniques described in Clackson et al.[26]

Humanized forms of the antibodies may be generated according to the methods known in the art such as chimerization or CDR grafting. Alternative methods for the production of humanized antibodies are well known in the art and are described in, e.g., EP-A1 0 239 400 and WO 90/07861. Human antibodies can also be derived by in vitro methods. Suitable examples include but are not limited to phage display, yeast display, and the like.

According the present invention "chimeric antibody" relates to antibodies comprising polypeptides from different species, such as, for example, mouse and human. The production of chimeric antibodies is described, for example, in WO 89/09622.

Monospecific antibodies are antibodies that all have affinity for the same antigen. Multispecific antibodies are antibodies that have affinity for several antigens. A bispecific antibody has affinity for two different antigens.

The term antibody includes "fragments" or "derivatives", which have at least one antigen binding site of the antibody. According to a preferred embodiment the antibody or fragment thereof may be a Fab fragment, a Fab' fragment, a F(ab') fragment, a Fv fragment, a diabody, a ScFv, a small modular immunopharmaceutical (SMIP), an affibody, an avimer, a nanobody, a domain antibody and/or single chains.

"Avimer" relates to a multimeric binding protein or peptide engineered using, for example, in vitro exon shuffling and phage display. Multiple binding domains are linked, resulting in greater affinity and specificity compared to single epitope immunoglobin domains.

"Nanobody" or single domain antibody relates to an antibody fragment consisting of a single monomeric variable antibody domain.

"Affibody" molecules are small high affinity proteins being engineered to bind specifically to a large number of target proteins.

The antibody of the invention may be preferably of the IgG1, IgG2, IgG3, IgG4, IgM, IgA1, IgA2, IgAsec, IgD, and IgE antibody-type. It will be appreciated that antibodies that are generated need not initially possess such an isotype but, rather the antibody as generated can possess any isotype and that the antibody can be isotype-switched.

The antibodies or antibody fragments of the invention are optionally deimmunized for therapeutic purposes.

In an especially preferred embodiment of the invention, the antibody is MP-RM-1, deposited at Deutsche Sammlung von Mikroorganismen and Zellkulturen (DSMZ) on 15 Oct. 2009 and designated DSM ACC3018.

According to a further preferred embodiment the antibody or fragment thereof may be produced from the hybridoma cell line DSM ACC3018 or a derivative thereof.

According to a preferred embodiment of the invention, the antibody or fragment produced from the hybridoma cell line DSM ACC3018 or a derivative thereof is a humanized antibody or fragment thereof. Preferably, this humanized antibody comprises at least one of the sequences 3-14 of the present invention. According to an especially preferred embodiment, the antibody is selected from the group cMP-RM-1 #1, cMP-RM-1 #2, cMP-RM-1 #3, cMP-RM-1 #4, hMP-RM-1 #5, hMP-RM-1 #6, hMP-RM-1 #7, hMP-RM-1 #8, hMP-RM-1 #9, hMP-RM-1 #10, hMP-RM-1 #11, hMP-RM-1 #12, hMP-RM-1 #13, hMP-RM-1 #14, hMP-RM-1 #15, hMP-RM-1 #16, hMP-RM-1 #17, hMP-RM-1 #18, hMP-RM-1 #19, hMP-RM-1 #20 (c, chimeric antibody; h, humanized antibody).

An especially preferred embodiment relates to an antibody which is selected from the group cMP-RM-1 #4, hMP-RM-1 #14, hMP-RM-1 #17 or hMP-RM-1 #20.

Another preferred embodiment relates to the group of antibodies consisting of hMP-RM-1 #6, hMP-RM-1 #7, hMP-RM-1 #8, hMP-RM-1 #9, hMP-RM-1 #10, hMP-RM-1 #11, hMP-RM-1 #12, hMP-RM-1 #19 and hMP-RM-1 #20. A particularly preferred group of antibodies comprises the antibodies hMP-RM-1 #6, hMP-RM-1 #10 and hMP-RM-1 #20.

It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level.

Thus, for diagnostic purposes, the antibody or antibody fragment of the invention may be labelled, i.e. coupled to a labelling group. Suitable labels include radioactive labels, fluorescent labels, suitable dye groups, enzyme labels, chromogenes, chemiluminescent groups, biotinyl groups, predetermined polypeptide epitopes recognized by a secondary reporter etc.

Those labelled antibodies or antibody fragments may be in particular used in immunohistochemistry assays or for molecular imaging in vivo.

For therapeutic purposes, the antibody or antibody fragment of the invention may be conjugated with a effector group, in particular a therapeutic effector group such as a radioactive group or a cytotoxic group.

Labelling groups or effector groups may be attached by spacer arms of various lengths to reduce potential steric hindrance.

According to another aspect, the present invention relates to a nucleic acid molecule encoding the antibody of the invention or fragment thereof or a nucleic acid capable of hybridizing thereto under stringent conditions. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions. In a particular preferred embodiment of the present invention, the nucleic acid molecule is a cDNA molecule.

The term "hybridizing under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

Another aspect of the invention relates to a vector comprising a nucleic acid molecule of the invention. Said vector may be, for example, a phage, plasmid, viral or retroviral vector. Retroviral vectors may be replication competent or replication defective. Preferably, the vector of the invention is an expression vector wherein the nucleic acid molecule is operatively linked to one or more control sequences allowing the transcription and optionally expression in prokaryotic and/or eukaryotic host cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extrachromosomally.

The host can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*.

The invention additionally relates to a method for the preparation of an antibody, comprising culturing the host of the invention under conditions that allow synthesis of said antibody and recovering said antibody from said culture.

A further aspect of the present invention relates to a pharmaceutical composition comprising the antibody of the invention or a fragment thereof, the nucleic acid molecule, the vector, the host of the invention or an antibody obtained by a method of the invention. The term "composition" as employed herein comprises at least one compound of the invention. Preferably, such a composition is a therapeutical/pharmaceutical or a diagnostic composition. The diagnostic composition of the invention may be used for assessing the onset or the disease status of a hyperproliferative disease as defined herein.

The composition preferably comprises an pharmaceutically acceptable carrier, diluent and/or excipient.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers, excipients and/or diluents can be formulated by well known conventional methods.

Administration of the suitable compositions may be effected by different ways, e.g., by intravenous, intraperitoneal, subcutaneous, intramuscular, topical, intradermal, intranasal or intrabronchial administration. Preferred is an intravenous, intramuscular and/or subcutaneous administration.

These pharmaceutical compositions can be administered to the subject at a suitable dose. The dosage regimen can be determined by the attending physician and clinical factors.

The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or' fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

According to an especially preferred embodiment the composition comprises a further active agent, such as a further antibody or antibody fragment.

Preferably the composition of the invention is used in combination with at least one further antineoplastic agent. Said combination is effective, for example, in inhibiting abnormal cell growth. Many antineoplastic agents are presently known in the art. In general the term includes all agents that are capable of prevention, alleviation and/or treatment of hyperproliferative disorders. Especially preferred are antineoplastic agents inducing apoptosis.

Preferably the antineoplastic agent is selected from the group consisting of antibodies, small molecules, antimetabolites, alkylating agents, topoisomerase inhibitors, microtubule-targeting agents, kinase inhibitors, protein synthesis inhibitors, immuno-therapeutics, hormones or analogs thereof, and/or mTOR inhibitors.

Specific examples of antineoplastic agents which can be used in combination with the antibodies provided herein include, for example, gefitinib, lapatinib, sunitinib, pemetrexed, bevacisumab, cetuximab, imatinib, alemtuzumab, trastuzumab, rituximab, erlotinib, bortezomib and the like, in particular trastuzumab. Other specific antineoplastic agents to be used in the compositions as described and claimed herein include for example, chemotherapeutic agents such as Paclitaxel, Anthracyclines, Fluoropirimidine, vinca alkaloids, platinum salts, in particular capecitabine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES).

The compositions of the invention may be administered in combination with a further therapeutic composition comprising an active agent as described above and/or irradiation and/or radiotherapy.

According to a preferred embodiment, the compositions of the invention are for the use in treating and/or preventing hyperproliferative diseases, in particular neoplastic diseases or cancer. The compositions may also be used for the manufacture of a medicament for treating and/or preventing hyperproliferative diseases, in particular neoplastic diseases or cancer.

A hyperproliferative disease as defined herein includes any neoplasia, i.e. any abnormal and/or uncontrolled new growth of tissue. The term "uncontrolled new growth of tissue" as used herein may depend upon a dysfunction and/or loss of growth regulation. A hyperproliferative disease includes tumor diseases and/or cancer, such as metastatic or invasive cancers.

The hyperproliferative disease is preferably selected from disorders associated with, accompanied by or caused by ErbB3 expression, overexpression or hyperactivity, such as cancer, in particular melanoma, breast cancer, ovarian cancer, renal carcinoma, gastrointestinal/colon cancer, lung cancer, clear cell carcinoma of the kidney and/or prostate cancer. In particular, for these tumors, it has been demonstrated a role of ErbB3 in promoting cancer development and growth, and, thus, the inhibition of this protein could give certain benefits.

The invention further relates to a method of treating a disease wherein the antibody of the invention is administered to a mammal and wherein said disease is correlated directly or indirectly with an abnormal level of expression or activity of ErbB3.

A further aspect of the present invention relates to a method of inhibiting EGF-like ligand mediated phosphorylation of ErbB3 in a subject, comprising administering to the subject an antibody or antigen binding portion thereof of as described above, in an amount sufficient to inhibit EGF-like mediated phosphorylation of ErbB3. "Phosphorylation of ErbB3" refers to the phosphorylation of amino acid residues, preferably tyrosine residues.

Yet another aspect of the present invention is directed to a method of diagnosing a cancer associated with ErbB3 in a subject, comprising
(a) contacting ex vivo or in vivo cells from the subject with an antibody or antigen binding portion thereof of any one of the preceding claims and
(b) measuring the level of binding to ErbB3 on the cells, wherein abnormally high levels of binding to ErbB3 indicate that the subject has a cancer associated with ErbB3.

In terms of the present invention, "abnormally high" means higher binding levels of ErbB3 compared to a healthy subject having no cancer.

Preferably the subject is an animal, more preferably a mammalian and in particular preferably a human.

EXAMPLES

Example 1

Production of the Monoclonal Antibody MP-RM-1

Four-weeks old Balb/c mice were immunized by intraperitoneal injection of live NIH/3T3 cells transfected with the human ErbB3 receptor. Seven days later, mice were given an additional intraperitoneal injection of the immunogen. After additional seven days, mice were boosted intravenously with the immunogen, and spleens were removed for cell fusion 3 days later. Somatic cell hybrids were prepared by fusion of immune splenocytes with the murine nonsecreting myeloma cell line NS-1. Hybridoma supernatants were selected on the basis of differential reactivity with LTR-ErbB3 transfected cells, but not with LTR-neo NIH/3T3. All positive hybridoma cell colonies were cloned twice by limiting dilution and further characterized. The selected monoclonal antibody, named MP-RM-1 (isotype IgG2a) was found to specifically recognize the extracellular domain of the ErbB3 receptor.

The hybridoma murine cell line producing MP-RM-1 antibody was deposited at the DSMZ (Deutsche Sammlung von Mikroorganismen and Zellkulturen) and designated DSM ACC3018.

Example 2

Effect of MP-RM-1 on ErbB3 Receptor Expression on the Surface of Breast Cancer Cells

Materials and Methods:

MDA-MB-435 human breast cancer cells were maintained on ice for 30 minutes with 10 µg/ml of MP-RM-1 and then returned to 37° C. At the indicated times, cells were trypsinized and stained with a fluorescein-labeled goat anti-mouse IgG antibody and analyzed by FACS.

Figure 1:
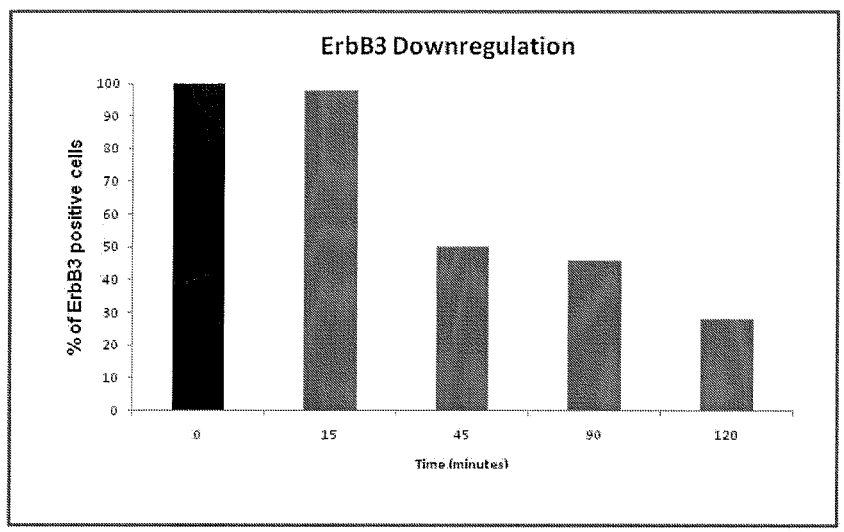
FIG. 1 shows that MP-RM-1 reduces the expression of ErbB3 receptor on the surface of breast cancer cells

Results:

MP-RM-1 decreases ErbB3 receptor expression on the cell surface in a time-dependent manner (FIG. 1).

Example 3

Effect of MP-RM-1 on Downregulation of the ErbB3 Receptor in Breast Cancer Cells

Materials and Methods:

MDA-MB-435 human breast cancer cells were grown in 0.2% FBS DMEM for 24 hours and then incubated in the presence or absence of 10 µg/ml of MP-RM-1 for 15, 60, 120 and 240 minutes. At the end of the incubation periods, cells were lysed and analyzed for ErbB3 and AKT protein levels by Western blotting with anti-ErbB3 and anti-AKT. The same filter was reprobed with anti-PLC γ-1 for a loading control.

Figure 2:
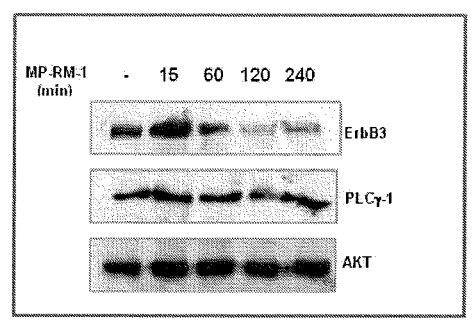
FIG. 2 shows that MP-RM-1 downregulates ErbB3 receptor in breast cancer cells.

Results:

MP-RM-1 induces downregulation of ErbB3 receptor after 120 minutes (FIG. 2).

Example 4

Effect of MP-RM-1 on ErbB3 Receptor Half-Life in Breast Cancer Cells

Materials and Methods:

MDA-MB-435 human breast cancer cells were grown in 0.2% FBS DMEM for 24 hours and then chased with the protein synthesis inhibitor cycloheximide at 10 µg/ml with or without MP-RM-1. Cells were lysed and analyzed for ErbB3 and AKT protein levels by Western blotting with anti-ErbB3 and anti-AKT. The same filter was reprobed with anti-PLC γ-1 or anti-Actin for a loading control.

Figure 3:
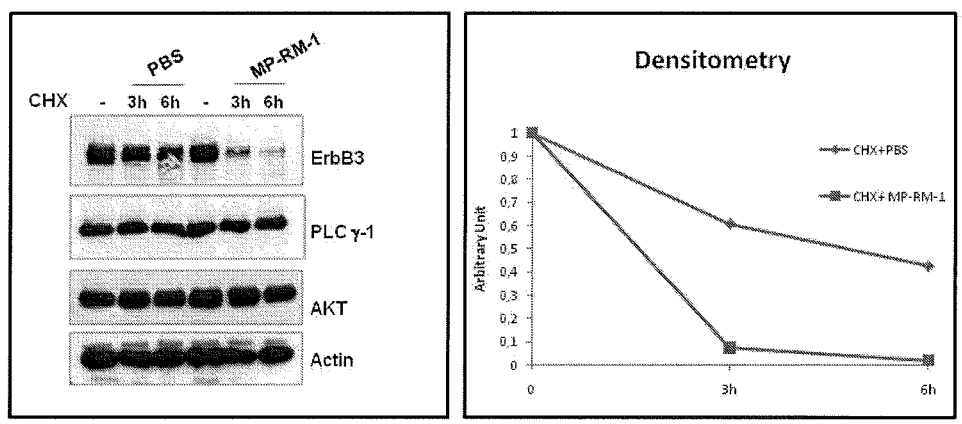
FIG. 3 shows that MP-RM-1 is able to reduce ErbB3 receptor half-life in MDA-MB-435 human breast cancer cells.

Results:

ErbB3 receptor half-life is markedly reduced in cycloheximide chased, MP-RM-1 treated MDA-MB-435 cells compared to PBS-treated control cells (FIG. 3).

Example 5

Effect of MP-RM-1 on ErbB3 Receptor Half-Life in Breast Cancer Cells

Materials and Methods:

SKBR-3 human breast cancer cells were grown in 0.2% FBS DMEM for 24 hours and then chased with the protein synthesis inhibitor cycloheximide at 10 µg/ml in the presence or absence of MP-RM-1. Cells were lysed and analyzed for ErbB3 levels by Western blotting with anti-ErbB3.

Figure 4:
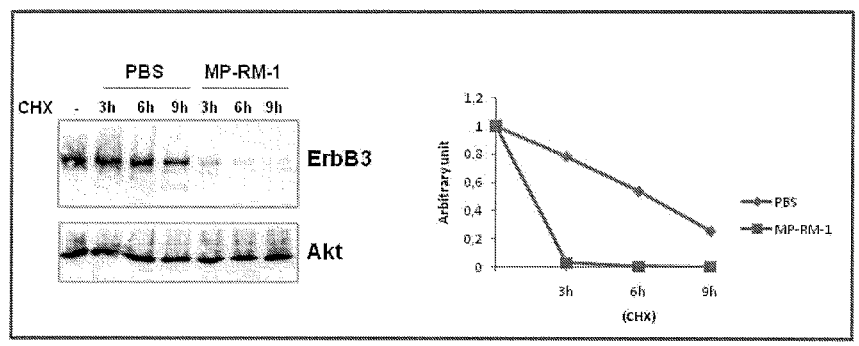
FIG. 4 shows that MP-RM-1 is able to reduce ErbB3 receptor half-life in SKBR-3 human breast cancer cells.

Results:

ErbB3 receptor half-life is markedly reduced in cycloheximide chased, MP-RM-1 treated SKBR-3 cells compared to the PBS treated control cells (FIG. 4).

Example 6

Effect of Chloroquine on ErbB3 Receptor Downregulation Induced by MP-RM-1

Figure 5:
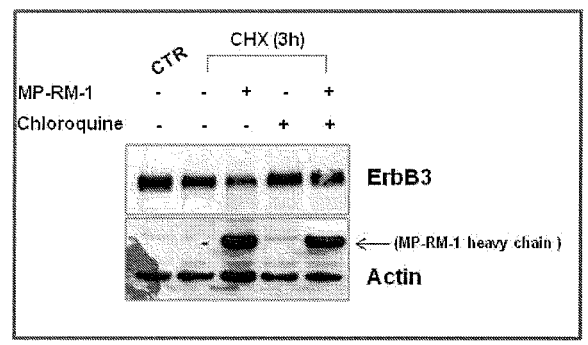
FIG. 5 shows that the effect MP-RM-1 on the reduction of the ErbB3 receptor half-life is blocked by the lysosome inhibitor chloroquine.

Materials and Methods:

MDA-MB-435 human breast cancer cells were grown on 0.2% FBS for 24 hours and chased for 3 hours with cycloheximide at 10 µg/ml. Cells were then incubated with MP-RM-1 in the presence or absence of chloroquine. After incubation, cells were lysed and analyzed for ErbB3 protein levels by Western blotting with anti-ErbB3. The same filter was reprobed with anti-Actin for a loading control Results:

ErbB3 receptor downregulation induced by MP-RM-1 is blocked by chloroquine (FIG. 5).

Example 7

Effect of MP-RM-1 on Ligand-Induced ErbB3 and AKT Phosphorylation in Breast and Melanoma Cancer Cells

Materials and Methods:

MDA-MB-435 human breast cancer cells, A375 and IR-8 human melanoma cells were grown in 0.2% FBS in DMEM or RPMI for 24 hours. Cells were incubated in the presence or absence of MP-RM-1 at 1 or 10 µg/ml for 2 hours and then stimulated with 10 ng/ml of NRG-1 for 5 minutes. After incubation, cells were lysed and analyzed for ErbB3, p-ErbB3, AKT, p-AKT, or p-Erks protein levels by Western blotting with anti-ErbB3, anti-p-ErbB3, anti-AKT, anti-p-AKT and anti-p-Erks. The same filter was reprobed with anti-Actin for a loading control.

Figure 6:
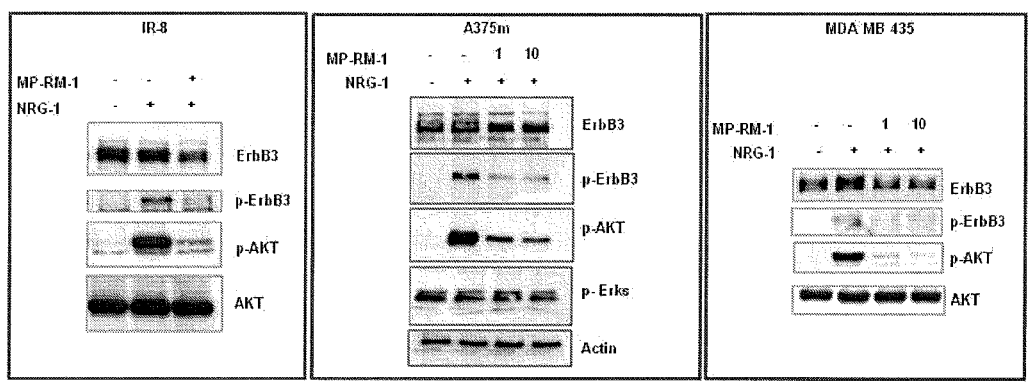
FIG. 6 shows that MP-RM-1 inhibits the phosphorylation of ErbB3 and AKT induced by the receptor ligand NRG-1 in MDA-MB-435 human breast cancer and IR-8 human melanoma cells.

Results:

Cells pre-treated with MP-RM-1 exhibit a dose-dependent inhibition of ErbB3 and AKT ligand-induced phosphorylation (FIG. 6).

Example 8

Effect of MP-RM-1 on Ligand-Induced ErbB3 and AKT Phosphorylation

Materials and Methods:

MDA-MB-435 human breast cancer cells were grown in 0.2% FBS DMEM for 24 hours and then stimulated with 10 ng/ml of NRG-1 for 5 minutes. Cells were then incubated with 10 µg/ml of MP-RM-1 for 15, 60 and 120 minutes before of NRG-1 stimulation. After incubation, cells were lysed and analyzed for ErbB3, p-ErbB3, AKT and p-AKT protein levels by Western blotting with anti-ErbB3, anti-p-ErbB3, anti-AKT and anti-p-AKT.

Figure 7:
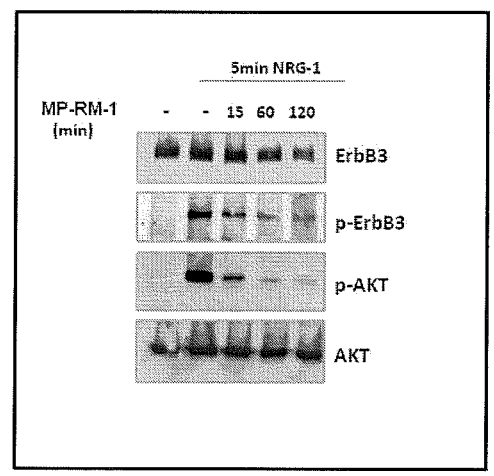
FIG. 7 shows that ligand-induced phosphorylation of ErbB3 and AKT is inhibited by MP-RM-1 in a time-dependent fashion.

Results:

Cells pre-treated with MP-RM-1 exhibit a time-dependent inhibition of ErbB3 and AKT ligand-induced phosphorylation (FIG. 7).

Example 9

Effect of MP-RM-1 on Ligand-Induced ErbB3 and AKT Phosphorylation

Materials and Methods:

MDA-MB-435 human breast cancer cells were grown in 0.2% FBS DMEM for 24 hours and then simultaneously stimulated with 10 ng/ml of NRG-1 and 10 µg/ml of MP-RM-1 for 5 minutes. After incubation, cells were lysed and analyzed for ErbB3, p-ErbB3 and p-AKT protein levels by Western blotting with anti-ErbB3, anti-p-ErbB3 and anti-p-AKT.

Figure 8:
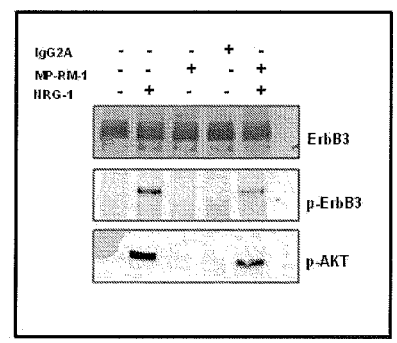
FIG. 8 shows that MP-RM-1 is able to antagonize the ligand-induced activation of ErbB3 and AKT.

Results:

5 minutes stimulation with MP-RM-1 does not induce ErbB3 and AKT phosphorylation, indicating that MP-RM-1 is not a receptor agonist. By contrast, ligand-induced ErbB3 and AKT phosphorylation is partially inhibited by MP-RM-1, indicating that MP-RM-1 is a partial receptor antagonist (FIG. 8).

Example 10

MP-RM-1 Internalization in MDA-MB-435 Breast Carcinoma Cells

Materials and Methods:

MDA-MB-435 human breast cancer cells were plated in 22×22 mm coverslips and grown in 0.2% FBS DMEM for 24 hours. Cells were then incubated with 10 µg/ml of MP-RM-1 for 30 minutes on ice and returned at 37° C. After 30 and 60 minutes, cells were fixed in 4% paraformaldehyde, permeabilized with 0.2% Triton-X100 in PBS and then stained with a fluorescein-labeled goat anti-mouse antibody (green staining), phalloydin (red staining). Cell nuclei were counterstained in blue. The yellow and the white arrows indicate MP-RM-1 localization on the cell membrane and in the cytoplasm, respectively.

Figure 9:
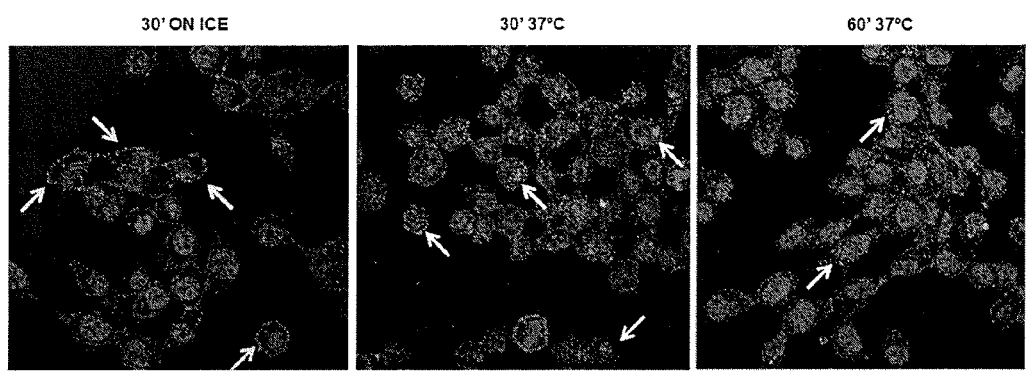
FIG. 9 shows that MP-RM-1 is rapidly (30 minutes) internalized into cells.

Results:

MDA MB 435 cells show goat anti mouse membrane positively (yellow arrows) after 30 minutes of MP-RM-1 incubation on ice indicating that MP-RM-1 antibody is completely localized on the plasma membrane. After 30 and 60 minutes 37° C. incubation the goat anti mouse signals is totally intracellular (white arrows) indicating that MP-RM-1 has been internalized by the cells (FIG. 9).

Example 11

Comparative Effect of MP-RM-1 and Trastuzumab on Ligand-Induced Activation of ErbB3 and AKT in Breast Cancer and Prostate Cells Materials and Methods:

MDA-MB-435 human breast cancer cells and DU 145 human prostate cancer cells were grown in 0.2% FBS RPMI for 24 hours and then stimulated with 10 ng/ml of NRG-1 for 5 minutes. Cells were then incubated for 2 hours with either MP-RM-1 at 1 or 10 µg/ml, or Trastuzumab at 10 µg/ml before ligand stimulation. After incubation, cells were lysed and analyzed for ErbB3, p-ErbB3, AKT, p-AKT and p-Erks protein levels by Western blotting with anti-ErbB3, anti-p-ErbB3, anti-AKT, anti-p-AKT and anti-p-Erks.

Figure 10:
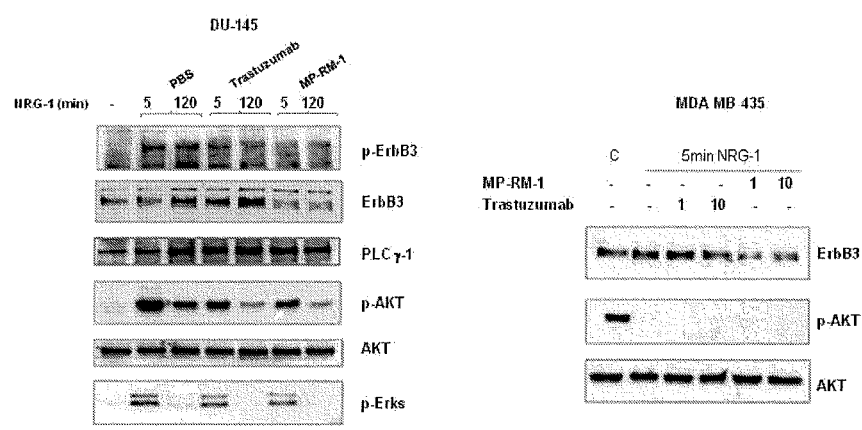
FIG. 10 compares the effect of MP-RM-1 and Trastuzumab on ligand-induced activation of ErbB3 and AKT in human breast and prostate cancer cells.

Results:

MP-RM-1 inhibits ligand induced ErbB3 and AKT phosphorylation at the same extent of Trastuzumab. However ErbB3 downregulation is induced by MP-RM-1, but not by Trastuzumab (FIG. 10).

Example 12

Effect of MP-RM-1 on MET/ErbB3/AKT Signalling Axis in MET-Amplified Gastric Cancer Cells Materials and Methods:

MKN-45 human gastric cancer cells were grown in 0.2% FBS DMEM for 24 hours. Cells were then exposed to MP-RM-1 at 1 and 10 µg/ml, or Trastuzumab at 10 µg/ml, or MET inhibitor SU11274 at 0.1, 1 and 10 µg/ml. Cells were then lysed and analyzed for ErbB3, p-ErbB3, AKT, p-AKT and p-MET protein levels by Western blotting with anti-ErbB3, anti-p-ErbB3, anti-AKT, anti-p-AKT and anti-p-MET.

Figure 11:
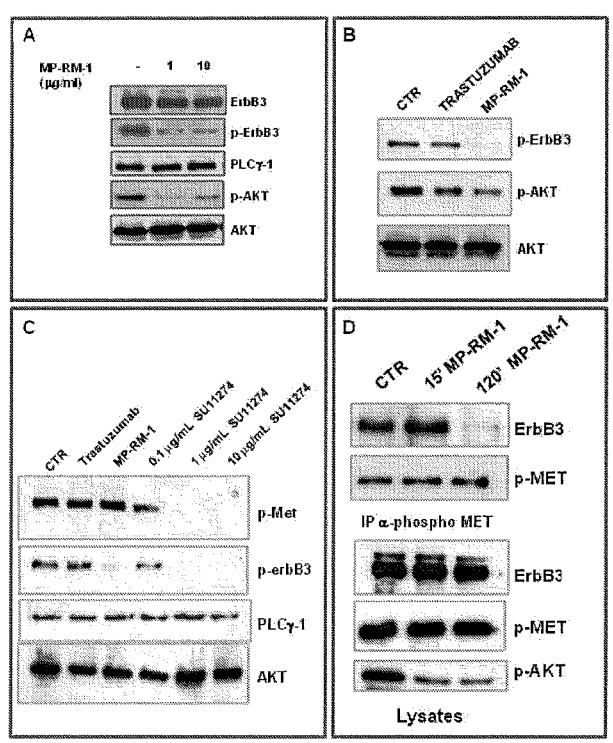
FIG. 11 shows that MP-RM-1 is able to inhibit basal ErbB3 and AKT phosphorylation in MET-amplified MKN-45 human gastric cancer cells.

Results:

MKN-45 cells show a ligand-independent, MET-dependent phosphorylation of ErbB3 receptor and AKT. MP-RM-1, but not Trastuzumab inhibits this basal activity. Moreover, MP-RM-1 is able to disrupt the ligand independent MET/ErbB3 association in vivo (FIG. 11).

Example 13

Effect of MP-RM-1 on Ligand-Induced Proliferation of Breast Cancer Cells

Materials and Methods:

MDA-MB-435 human breast cancer cells were grown in 0.2% FBS RPMI for 24 hours and then incubated with 10 ng/ml of NRG-1 for 48 hours in the presence or absence of MP-RM-1 at 1 or 10 µg/ml. At the end of the incubation, cells were trypsinized and counted.

Figure 12:
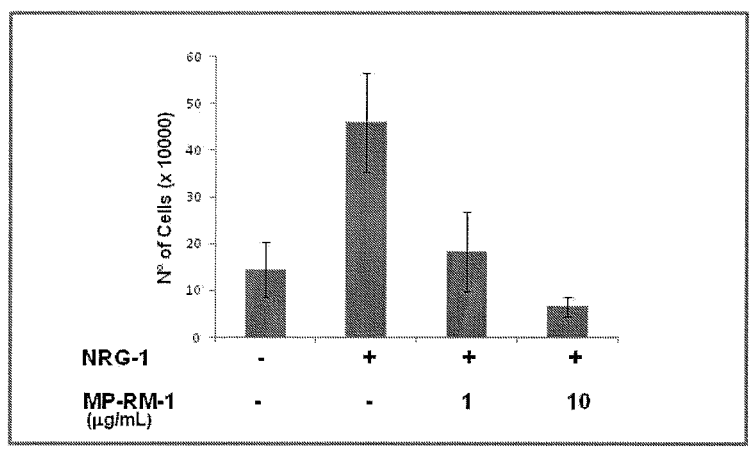
FIG. 12 shows that MP-RM-1 inhibits ligand-induced proliferation in MDA-MB-435 human breast cancer cells.

Results:

MP-RM-1 inhibits, in a dose-dependent manner, ligand-induced proliferation of MDA-MB-435 cells (FIG. 12).

Example 14

Effect of MP-RM-1 on Prostate Cancer Xenografts

Materials and Methods:

Human prostate cancer xenografts were established by injecting subcutaneously $5 \times 10^6$ DU145 cells in 5-week old CD1 nude mice. When xenografts were palpable, mice were separated into two groups of 10 animals. The two groups had comparable mean tumor volume. One group received intraperitoneal injection twice per week of 20 mg/kg MP-RM-1 in PBS buffer, whereas the other received PBS only (control group). Tumor volume was monitored every day by a caliper. Error bars indicated SE in each group. * denotes significant difference (P=0.01)** denotes significant difference (P=0.006) between MP-RM-1 treated mice and PBS-treated (control) mice.

Figure 13:
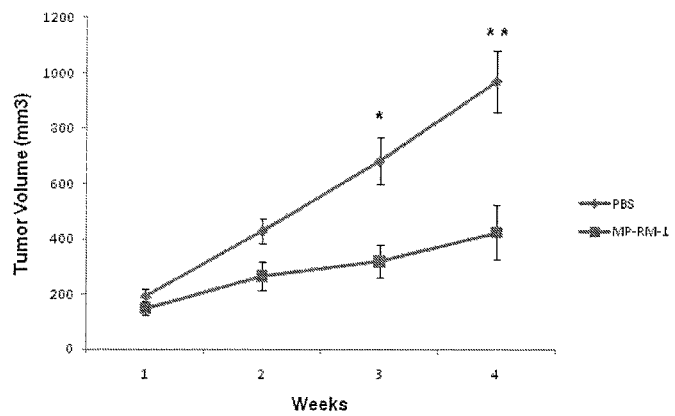
FIG. 13 shows that MP-RM-1 inhibits the growth of DU145 human prostate cancer xenografts

Results:

MP-RM-1 treated mice show up to 60% reduction of tumor volume compared to the control mice (0.42 cm$^3$ vs 0.96 cm$^3$) (FIG. 13).

Example 15

In Vivo Effect of MP-RM-1 on ErbB3 Downregulation and AKT Phosphorylation in Melanoma Xenografts Materials and Methods:

Nude mice harboring IR-8 melanoma xenografts were treated or not (U) with 200 μg of MP-RM-1. After 4 hours, 16 hours, and 24 hours, tumors were collected and homogenized with a Polytron homogenizer in a lysis buffer (w:v, 1:10) containing 50 mM Tris-HCl (pH 7.4), 5 mM EDTA, 0.1% NP-40, 250 mM NaCl, 50 mM NaF in the presence of leupeptine, pepstatine, aprotinin and phenyl-methyl-sulfonyl-fluoride. Homogenates were centrifuged at 13,000 rpm for 10 min at 4° C. Aliquots of the supernatants were analyzed for ErbB3, AKT and p-AKT protein levels by Western blotting with anti-ErbB3, anti-AKT, anti-p-AKT. The same filter was reprobed with anti-PLC γ-1 for a loading control.

Figure 14:
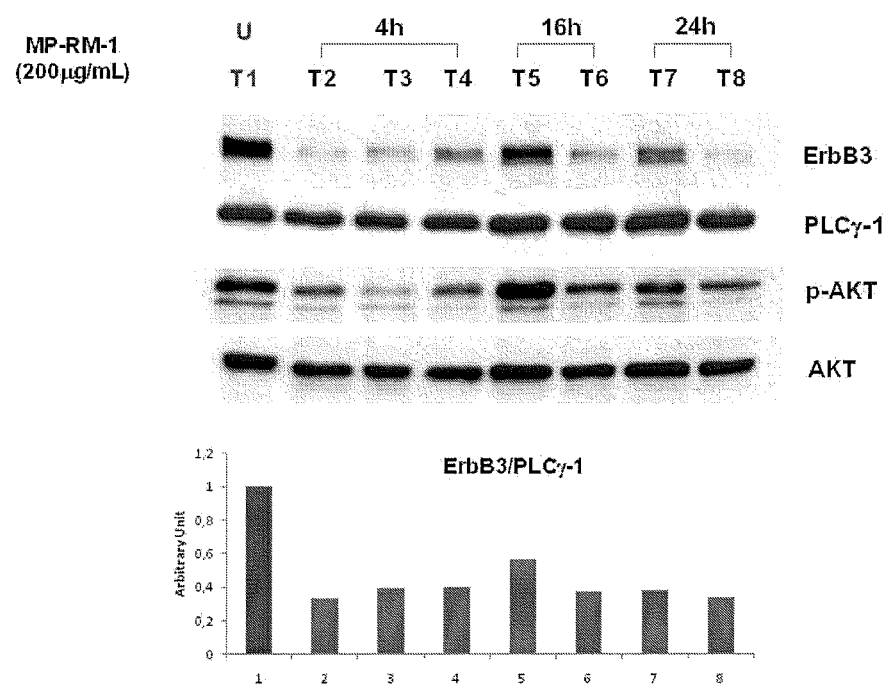
FIG. 14 shows that as soon as 4 hours after injection into mice, MP-RM-1 induces ErbB3 downregulation and inhibits AKT activation in IR-8 human melanoma xenografts.

Results:

MP-RM-1 induces ErbB3 downregulation and inhibits AKT phosphorylation in melanoma xenografts starting 4 hours after injection to mice (FIG. 14).

Example 16

Production of Chimeric and Humanized Versions of the MP-RM-1 Antibody

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following published procedures (27-29), in particular by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some framework region (FR) residues are substituted by residues from analogous sites in rodent antibodies.

To produce chimeric and humanized versions of the MP-RM-1 antibody, hybridoma cells producing the MP-RM-1 antibody (deposited at DSMZ, and designed DSM ACC3018) were expanded, total RNA extracted and RT-PCR performed to clone and sequence the variable regions of the antibody using conventional procedures (e.g., by using oligonucleotide probes that are capable of binding specifically to genes encoding the heavy and light chains of murine antibodies).

Based on sequence information of the variable region of MP-RM-1 antibody, 20 different variants of said region have been obtained by gene synthesis using standard procedures.

For antibody chimerization, the murine constant regions were replaced with the human constant regions. Two chimeric versions of the heavy chain (HC) were made in an IgG1 context and two chimeric versions of the heavy chain (HC) in an IgG3 context;

For antibody humanization, Complementarity Determining Regions (CDRs) from the murine were grafted in to a human antibody framework.

Sixteen humanized versions of the heavy chain (HC) were made in an IgG1 and LC-kappa context. Each version is characterized by specific point mutations in the FR.

Sequence Information:

---

CHIMERIC SEQUENCES

SEQ ID NO: 3: CHIMERIC IgG1 HC SEQUENCE
mnfglrliflvltlkgvqcdvqLVESGGDLVKPGGSLKLSCVVSGFTFSTYGMSWVRQTPDRRLEWVATIS
HGDGYTYYPDSVKGRFTISRDNAKNTLHLQMSSLKSEDTAMYYCARHGDYDDDYYAMDYWGQGTSVTFSsa
stkgpsvfplapssktsggtaalgclvkdyfpepvtvswnsgaltsgvhtfpavlqssglyslssvvtvp
ssslgtqtyicnvnhkpsntkvdkrvepkscdkthtcppcpapellggpsvflfppkpkdtlmisrtpevt
cvvvdvshedpevkfnwyvdgvevhnaktkpreeqynstyrvvsvltvlhqdwlngkeykckvsnkalpap
iektiskakgqprepqvytlppsreemtknqvsltclvkgfypsdiavewesngqpennykttppvldsdg
sfflyskltvdksrwqqgnvfscsvmhealhnhytqkslslspgk SEQ ID NO: 4: CHIMERIC IgG2 HC SEQUENCE
mnfglrliflvltlkgvqcdvqLVESGGDLVKPGGSLKLSCVVSGFTFSTYGMSWVRQTPDRRLEWVATIS
HGDGYTYYPDSVKGRFTISRDNAKNTLHLQMSSLKSEDTAMYYCARHGDYDDDYYAMDYWGQGTSVTFSsa
stkgpsvfplapcsrstsestaalgclvkdyfpepvtvswnsgaltsgvhtfpavlqssglyslssvvtvp
ssnfgtqtytcnvdhkpsntkvdktverkccvecppcpappvagpsvflfppkpkdtlmisrtpevtcvvv
dvshedpevqfnwyvdgmevhnaktkpreeqfnstfrvvsvltvvhqdwlngkeykckvsnkglpapiekt
isktkgqprepqvytlppsreemtknqvsltclvkgfypsdisvewesngqpennykttppmldsdgsffl
yskltvdksrwqqgnvfscsvmhealhnhytqkslslspgk SEQ ID NO: 5: CHIMERIC IgG3 HC SEQUENCE
mnfglrliflvltlkgvqcdvqLVESGGDLVKPGGSLKLSCVVSGFTFSTYGMSWVRQTPDRRLEWVATIS
HGDGYTYYPDSVKGRFTISRDNAKNTLHLQMSSLKSEDTAMYYCARHGDYDDDYYAMDYWGQGTSVTFSsa
stkgpsvfplapcsrstsggtaalgclvkdyfpepvtvswnsgaltsgvhtfpavlqssglyslssvvtvp
ssslgtqtytcnvnhkpsntkvdkrvelktplgdtthtcprcpepkscdtpppcprcpepkscdtpppcpr
cpapellggpsvflfppkpkdtlmisrtpevtcvvvdvshedpevqfkwyvdgvevhnaktkpreeqynst
frvvsvltvlhqdwlngkeykckvsnkalpapiektisktkgqprepqvytlppsreemtknqvsltclvk
gfypsdiavewessgqpennynttppmldsdgsfflyskltvdksrwqqgnifscsvmhealhnrftqksl
slspgk SEQ ID NO: 6: CHIMERIC LC KAPPA SEQUENCE
mesqtqvlisllfwvsgtcgdIVMTQSPSSLTVIAGEKVTMSCKS<u>SQSLLNSGNQKNYL</u>TWYQQKPGQPPK
LLIY<u>WASTRES</u>GVPDRFTGSGSGTDFTLTISSVQAEDLAVYYC<u>QNEYTYPLT</u>FGAGTKLEI*krtvaapsvf
ifppsdeqlksgtasvvcllnnfypreakvqwkvdnalqsgnsqesvteqdskdstyslsstltlskadye
khkvyacevthqglsspvtksfnrgec*

SEQ ID NO: 7: CHIMERIC LC LAMBDA SEQUENCE
mesqtqvlisllfwvsgtcgdIVMTQSPSSLTVIAGEKVTMSCKS<u>SQSLLNSGNQKNYL</u>TWYQQKPGQPPK
LLIY<u>WASTRES</u>GVPDRFTGSGSGTDFTLTISSVQAEDLAVYYC<u>QNEYTYPLT</u>FGAGTKLTVL*gqpkaapsv
tlfppsseelqankatlvclisdfypgavtvawkadsspvkagvetttpskqsnnkyaassylsltpeqwk
shrsyscqvthegstvektvaptecs*

HUMANIZED SEQUENCES

SEQ ID NO: 8: HUMANIZED IgG1 HC SEQUENCE 1
mnfglrliflvltlkgvqcdvqLVESGGGLVQPGGSLRLSCAASGFTFS<u>TYGMS</u>WVRQTPDKRLEWVA<u>TIS
HGDGYTYYPDSVKG</u>RFTISRDNAKNTLYLQMSSLKSEDTAMYYCAR<u>HGDYDDDYYAMD</u>YWGQGTLVTVS*sa
stkgpsvfplapssskstsggtaalgclvkdyfpepvtvswnsgaltsgvhtfpavlqssglyslssvvtvp
ssslgtqtyicnvnhkpsntkvdkrvepkscdkthtcppcpapellggpsvflfppkpkdtlmisrtpevt
cvvvdvshedpevkfnwyvdgvevhnaktkpreeqynstyrvvsvltvlhqdwlngkeykckvsnkalpap
iektiskakgqprepqvytlppsreemtknqvsltclvkgfypsdiavewesngqpennykttppvldsdg
sfflyskltvdksrwqqgnvfscsvmhealhnhytqkslslspgk*

SEQ ID NO: 9: HUMANIZED IgG1 HC SEQUENCE 2
mnfglrliflvltlkgvqcdvqLVESGGGLVQPGGSLRLSCAVSGFTFS<u>TYGMS</u>WVRQAPGKGLEWVA<u>TIS
HGDGYTYYPDSVKG</u>RFTISRDNSKNTLYLQMNSLRAEDTAVYYCAR<u>HGDYDDDYYAMD</u>YWGQGTLVTVS*sa
stkgpsvfplapssskstsggtaalgclvkdyfpepvtvswnsgaltsgvhtfpavlqssglyslssvvtvp
ssslgtqtyicnvnhkpsntkvdkrvepkscdkthtcppcpapellggpsvflfppkpkdtlmisrtpevt
cvvvdvshedpevkfnwyvdgvevhnaktkpreeqynstyrvvsvltvlhqdwlngkeykckvsnkalpap
iektiskakgqprepqvytlppsreemtknqvsltclvkgfypsdiavewesngqpennykttppvldsdg
sfflyskltvdksrwqqgnvfscsvmhealhnhytqkslslspgk*

SEQ ID NO: 10: HUMANIZED IgG1 HC SEQUENCE 3
mnfglrliflvltlkgvqcdvqLVESGGDLVKPGGSLKLSCVASGFTFS<u>TYGMS</u>WVRQTPDKRLEWVA<u>TIS
HGDGYTYYPDSVKG</u>RFTISRDNAKNTLYLQMSSLKSEDTAMYYCAR<u>HGDYDDDYYAMD</u>YWGQGTTVTVS*sa
stkgpsvfplapssskstsggtaalgclvkdyfpepvtvswnsgaltsgvhtfpavlqssglyslssvvtvp
ssslgtqtyicnvnhkpsntkvdkrvepkscdkthtcppcpapellggpsvflfppkpkdtlmisrtpevt
cvvvdvshedpevkfnwyvdgvevhnaktkpreeqynstyrvvsvltvlhqdwlngkeykckvsnkalpap
iektiskakgqprepqvytlppsreemtknqvsltclvkgfypsdiavewesngqpennykttppvldsdg
sfflyskltvdksrwqqgnvfscsvmhealhnhytqkslslspgk*

SEQ ID NO: 11: HUMANIZED IgG1 HC SEQUENCE 4
mnfglrliflvltlkgvqcdvqLVESGGDLVKPGGSLKLSCVASGFTFS<u>TYGMS</u>WVRQTPDRRLEWVA<u>TIS
HGDGYTYYPDSVKG</u>RFTISRDNAKNTLHLQMSSLKSEDTAMYYCAR<u>HGDYDDDYYAMD</u>YWGQGTTVTVS*sa
stkgpsvfplapssskstsggtaalgclvkdyfpepvtvswnsgaltsgvhtfpavlqssglyslssvvtvp
ssslgtqtyicnvnhkpsntkvdkrvepkscdkthtcppcpapellggpsvflfppkpkdtlmisrtpevt
cvvvdvshedpevkfnwyvdgvevhnaktkpreeqynstyrvvsvltvlhqdwlngkeykckvsnkalpap
iektiskakgqprepqvytlppsreemtknqvsltclvkgfypsdiavewesngqpennykttppvldsdg
sfflyskltvdksrwqqgnvfscsvmhealhnhytqkslslspgk*

SEQ ID NO: 12: HUMANIZED LC KAPPA SEQUENCE 1
mesqtqvlisllfwvsgtcgdIVMTQSPDSLAVSLGERATINCKS<u>SQSLLNSGNQKNYL</u>TWYQQKPGQPPK
LLIY<u>WASTRES</u>GVPDRFSGSGSGTDFTLTISSLQAEDVAVYYC<u>QNEYTYPLT</u>FGGGTKLEI*krtvaapsvf
ifppsdeqlksgtasvvcllnnfypreakvqwkvdnalqsgnsqesvteqdskdstyslsstltlskadye
khkvyacevthqglsspvtksfnrgec*

SEQ ID NO: 13: HUMANIZED LC KAPPA SEQUENCE 2
mesqtqvlisllfwvsgtcgdIQMTQSPSSLSASVGDRVTITCKS<u>SQSLLNSGNQKNYL</u>TWYQQKPGKAPK
LLIY<u>WASTRES</u>GVPSRFSGSGSGTDFTLTISSLQPEDFATYYC<u>QNEYTYPLT</u>FGQGTKVEI*krtvaapsvf
ifppsdeqlksgtasvvcllnnfypreakvqwkvdnalqsgnsqesvteqdskdstyslsstltlskadye
khkvyacevthqglsspvtksfnrgec*

SEQ ID NO: 14: HUMANIZED LC KAPPA SEQUENCE 3
mesqtqvlisllfwvsgtcgdIVMTQSPDSLTVSLGERATINCKS<u>SQSLLNSGNQKNYL</u>TWYQQKPGQPPK
LLIY<u>WASTRES</u>GVPDRFSGSGSGTDFTLTISSVQAEDVAVYYC<u>QNEYTYPLT</u>FGGGTKLEL*krtvaapsvf
ifppsdeqlksgtasvvcllnnfypreakvqwkvdnalqsgnsqesvteqdskdstyslsstltlskadye
khkvyacevthqglsspvtksfnrgec*

SEQ ID NO: 15: HUMANIZED LC KAPPA SEQUENCE 4
mesqtqvlisllfwvsgtcgdIVMTQSPSSLTVSLGERATMSCKS<u>SQSLLNSGNQKNYL</u>TWYQQKPGQPPK
LLIY<u>WASTRES</u>GVPDRFSGSGSGTDFTLTISSVQAEDVAVYYC<u>QNEYTYPLT</u>FGGGTKLEL*krtvaapsvf
ifppsdeqlksgtasvvcllnnfypreakvqwkvdnalqsgnsqesvteqdskdstyslsstltlskadye
khkvyacevthqglsspvtksfnrgec*

Signal peptide in lower case (non italic)
Variable regions in capital letters, CRDs underlined
Constant regions in lower case italics
Point mutations in bold The 4 chimeric and the 16 humanized synthetic genes were placed into the pcDNA3.1 plasmid expression vector, and then transfected into Chinese Hamster Ovary-S (CHO-S) cells to obtain the synthesis of the monoclonal antibodies. Table 1 shows the 20 different vector combinations and the relative antibodies names.

TABLE 1

Vector combination of the 20 different variants of the MP-RM-1 antibody

| Vector combination | Antibody name |
| --- | --- |
| pCDNA3.1 HC-IgG1 CHIM + pCDNA3.1 LC-kappa CHIM | cMP-RM-1 #1 |
| pCDNA3.1 HC-IgG1 CHIM + pCDNA3.1 LC-lamda CHIM | cMP-RM-1 #2 |
| pCDNA3.1 HC-IgG3 CHIM + pCDNA3.1 LC-kappa CHIM | cMP-RM-1 #3 |
| pCDNA3.1 HC-IgG3 CHIM + pCDNA3.1 LC-lamda CHIM | cMP-RM-1 #4 |
| pCDNA3.1 HC-IgG1 HU1 + pCDNA3.1 LC-kappa HU1 | hMP-RM-1 #5 |
| pCDNA3.1 HC-IgG1 HU1 + pCDNA3.1 LC-kappa HU2 | hMP-RM-1 #6 |
| pCDNA3.1 HC-IgG1 HU1 + pCDNA3.1 LC-kappa HU3 | hMP-RM-1 #7 |
| pCDNA3.1 HC-IgG1 HU1 + pCDNA3.1 LC-kappa HU4 | hMP-RM-1 #8 |
| pCDNA3.1 HC-IgG1 HU2 + pCDNA3.1 LC-kappa HU1 | hMP-RM-1 #9 |
| pCDNA3.1 HC-IgG1 HU2 + pCDNA3.1 LC-kappa HU2 | hMP-RM-1 #10 |
| pCDNA3.1 HC-IgG1 HU2 + pCDNA3.1 LC-kappa HU3 | hMP-RM-1 #11 |
| pCDNA3.1 HC-IgG1 HU2 + pCDNA3.1 LC-kappa HU4 | hMP-RM-1 #12 |
| pCDNA3.1 HC-IgG1 HU3 + pCDNA3.1 LC-kappa HU1 | hMP-RM-1 #13 |
| pCDNA3.1 HC-IgG1 HU3 + pCDNA3.1 LC-kappa HU2 | hMP-RM-1 #14 |
| pCDNA3.1 HC-IgG1 HU3 + pCDNA3.1 LC-kappa HU3 | hMP-RM-1 #15 |
| pCDNA3.1 HC-IgG1 HU3 + pCDNA3.1 LC-kappa HU4 | hMP-RM-1 #16 |
| pCDNA3.1 HC-IgG1 HU4 + pCDNA3.1 LC-kappa HU1 | hMP-RM-1 #17 |
| pCDNA3.1 HC-IgG1 HU4 + pCDNA3.1 LC-kappa HU2 | hMP-RM-1 #18 |
| pCDNA3.1 HC-IgG1 HU4 + pCDNA3.1 LC-kappa HU3 | hMP-RM-1 #19 |
| pCDNA3.1 HC-IgG1 HU4 + pCDNA3.1 LC-kappa HU4 | hMP-RM-1 #20 | c, chimeric antibody; h, humanized antibody

Initial Screening for Antibodies with the Desired Properties

The supernatants containing the 20 different antibody variants were tested for their ability to inhibit ligand-induced ErbB3 and Akt phosphorylation and to promote ErbB3 downregulation in IR-8 human melanoma cells. The inhibitory effect of the variants on phosphorylation were evaluated in a long-term assay (treatment of the cells with the antibody variants at 10 µg/ml for 2 hours before NRG-1 stimulation) or in a short-term assay (co-exposure to the antibody variants and NRG-1 for 5 min). The results indicate that 4 antibody variants, i.e., cMP-RM-1 #1, hMP-RM-1 #6, hMP-RM-1 #10, hMP-RM-1 #20 were the most active in inhibiting ErbB3 and AKT phosphorylation and ErbB3 downregulation both in a long-term and a short-term assay (Table 2).

TABLE 2

Screening of the MP-RM-1 antibody variants

| AMP-RM-1 antibody variants | Isotype | Inhibitory Effect (LT)[1] | Inhibitory Effect (ST)[2] | Down-regulation[3] |
| --- | --- | --- | --- | --- |
| cMP-RM-1 #1 | IgG1 | +++ | ++++ | +++ |
| cMP-RM-1 #2 | IgG1 | +++ | + | ++ |
| cMP-RM-1 #3 | IgG3 | +++ | + | ++ |
| cMP-RM-1 #4 | IgG3 | ++++ | +/− | + |
| hMP-RM-1 #5 | IgG1 | +++ | ++ | + |
| hMP-RM-1 #6 | IgG1 | +++ | ++++ | +++ |
| hMP-RM-1 #7 | IgG1 | +++ | ++++ | ++ |
| hMP-RM-1 #8 | IgG1 | +++ | ++++ | ++ |
| hMP-RM-1 #9 | IgG1 | +++ | ++++ | ++ |
| hMP-RM-1 #10 | IgG1 | +++ | ++++ | +++ |
| hMP-RM-1 #11 | IgG1 | +++ | ++++ | ++ |
| hMP-RM-1 #12 | IgG1 | +++ | ++++ | ++ |
| hMP-RM-1 #13 | IgG1 | +++ | ++ | ++ |
| hMP-RM-1 #14 | IgG1 | ++++ | ++ | ++ |
| hMP-RM-1 #15 | IgG1 | +++ | ++ | ++ |
| hMP-RM-1 #16 | IgG1 | +++ | + | ++ |
| hMP-RM-1 #17 | IgG1 | ++++ | ++ | ++ |
| hMP-RM-1 #18 | IgG1 | +++ | ++ | + |
| hMP-RM-1 #19 | IgG1 | +++ | ++++ | ++ |
| hMP-RM-1 #20 | IgG1 | ++++ | ++++ | ++ |

[1]Refers to the phosphorylation status of ErbB3 and Akt of IR-8 cells that were incubated for 2 hours with the antibody variant after stimulation for 5 min with NRG-1;
[2]Refers to the phosphorylation status of ErbB3 and AKT of IR-8 cells that were incubated simultaneously with the antibody variant and NRG-1 for 5 min;
[3]Refers to the ability of the antibody variant to promote ErbB3 downregulation as evaluated by western blotting and FACS analysis.

On the basis of these results, the 4 antibody variants cMP-RM-1 #1, hMP-RM-1 #6, hMP-RM-1 #10, and hMP-RM-1 #20 were selected, purified by means of Protein A capture (HiTrap Protein A HP, GE Healthcare), and further tested for their ability to promote ErbB3 receptor internalization, ErbB3 receptor down-regulation as well as to inhibit in vitro and in vivo growth of human tumor cells.

Example 17

Effect of Chimeric and Humanized MP-RM-1 Antibody Variants on ErbB3 Receptor Expression on the Surface of Human Melanoma Cells Materials and Methods:

IR-8 human melanoma cells were maintained on ice for 30 minutes in the presence of 10 µg/ml of chimeric (cMP-RM-1 #1) or humanized (hMP-RM-1 #6, hMP-RM-1 #10, hMP-RM-1 #20) MP-RM-1 antibody variants and then returned to 37° C. for 60 minutes. Cells were harvested and stained with a fluorescein-labeled goat anti-human IgG antibody and analyzed by FACS.

Figure 15:
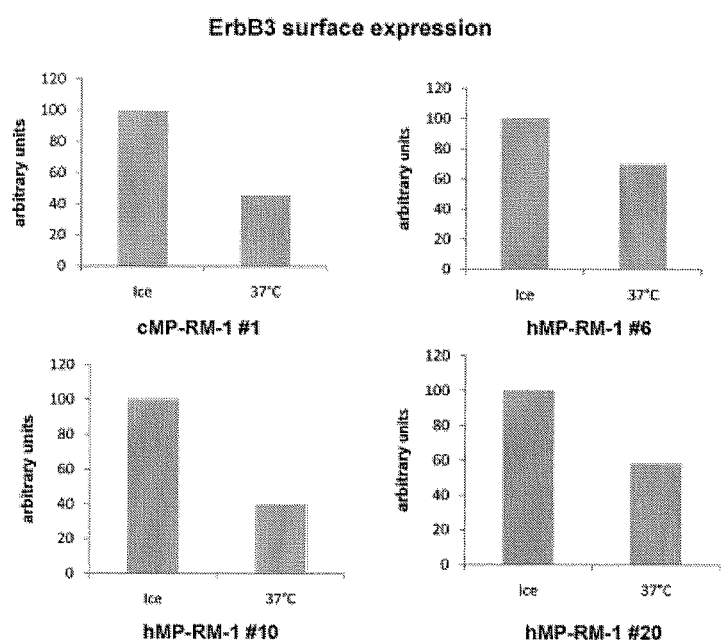
FIG. 15 shows that treatment of IR-8 human melanoma cells with cMP-RM-1 #1, hMP-RM-1 #6, hMP-RM-1 #10, hMP-RM-1 #20 MP-RM-1 antibody variants reduces the expression of ErbB3 receptor on cell surface.

Results:

Chimeric and humanized MP-RM-1 antibody variants induce a decrease of ErbB3 receptor expression on the surface of IR-8 human melanoma cells (FIG. 15).

Example 18

Internalization of hMP-RM-1 #6 in Human Melanoma Cells

Materials and Methods:

IR-8 human melanoma cells were plated in 15×15 mm coverslips and grown in 0.2% FBS in RPMI for 24 hours. Cells were then incubated with 10 µg/ml of the humanized MP-RM-1 #6 for 30 minutes on ice and returned at 37° C. After 30 minutes, cells were fixed in 4% paraformaldehyde, permeabilized with 0.2% Triton-X100 in PBS and then stained with a fluorescein-labeled goat anti-human antibody (green), phalloidin (red). Cell nuclei were counterstained in blue. The green staining indicate humanized MP-RM-1#6 antibody localization.

Figure 16:
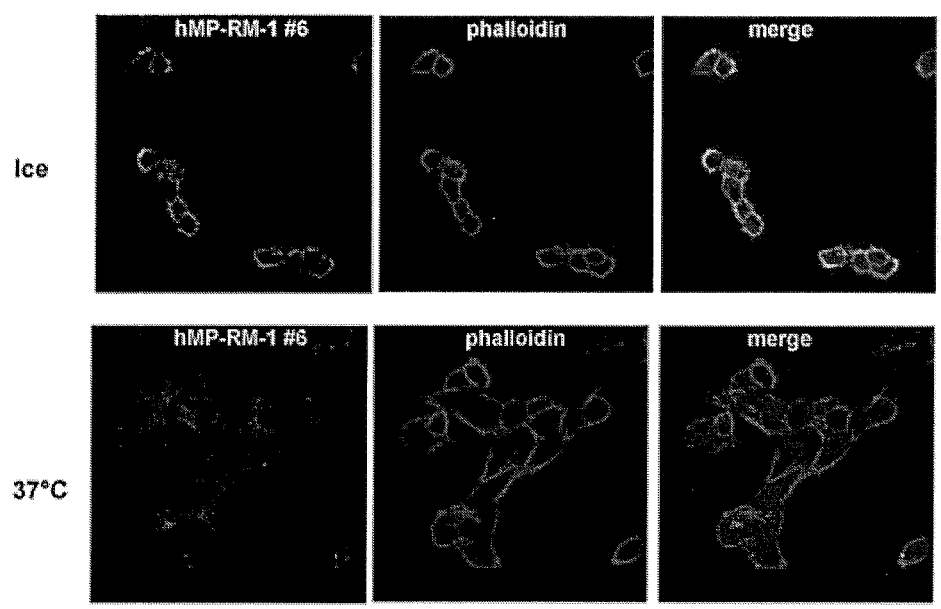
FIG. 16 shows that the humanized variant hMP-RM-1 #6 is rapidly (30 minutes) internalized into the cells.

Results:

In IR-8 human melanoma cells maintained in ice, hMP-RM-1 #6 antibody variant localizes on cell membrane (green ring). After shifting cells at 37° C. for 30 minutes, the antibody is totally localized intracellularly, indicating internalization (FIG. 16). Similar results have been obtained with cMP-RM-1 #1, hMP-RM-1 #10, and hMP-RM-1 #20 (not shown).

Example 19

Effect of Chimeric and Humanized MP-RM-1 Antibody Variants on ErbB3 Receptor Half-Life in Human Melanoma Cells Materials and Methods:

IR-8 human melanoma cells were grown in 0.2% FBS in RPMI for 24 hours and then chased with the protein synthesis inhibitor cycloheximide (CHX) at 10 µg/ml in the presence or absence of cMP-RM-1 #1, hMP-RM-1 #6, hMP-RM-1 #10 or hMP-RM-1 #20 antibody variants. Cells were lysed and analyzed for p-ErbB3 protein levels by Western blotting with an anti-p-ErbB3 specific antibody. The same filter was re-probed with anti-AKT for a loading control.

Figure 17:
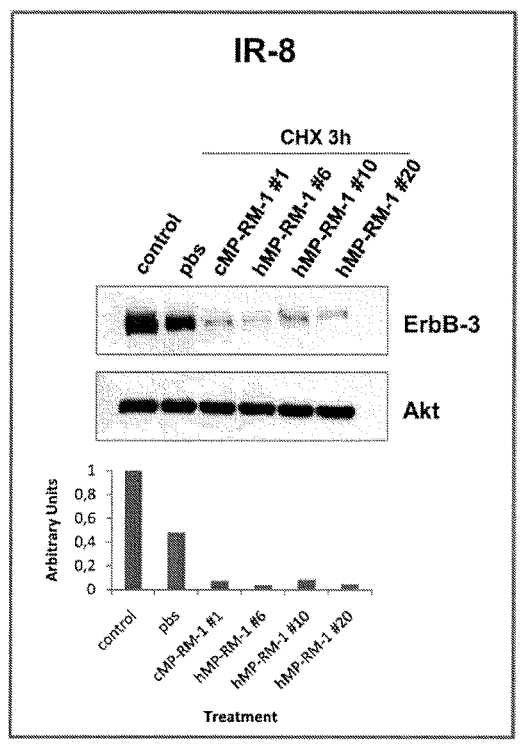
FIG. 17 shows the effect of the chimeric variant cMP-RM-1 #1, and the humanized variants hMP-RM-1 #6, hMP-RM-1 #10, hMP-RM-1 #20 antibody variants on ErbB3 half-life in IR-8 human melanoma cells.

Results:

In cycloheximide chased IR-8 human melanoma cells, exposure to the antibody variants markedly reduces ErbB3 receptor half-life as compared to PBS-exposed control cells (FIG. 17).

Example 20

Effect of Chimeric and Humanized MP-RM-1 Antibody Variants on ErbB3 and AKT Phosphorylation and ErbB3 Receptor Down-Regulation in Human Ovarian and Gastric Cancer Cells Materials and Methods:

(A) OVCAR-8 human ovarian cancer cells were grown in 0.2% FBS in RPMI for 24 hours. Cells were then pre-treated for 2 hours with cMP-RM-1 #1, hMP-RM-1 #6, hMP-RM-1 #10 or hMP-RM-1 #20 antibody variants at 10 µg/ml and stimulated for 10 minutes with ng/ml of NRG-1 10. Cells were lysed and analyzed for ErbB3, p-ErbB3, AKT, p-AKT levels by Western blotting using anti-ErbB3, anti-p-ErbB3, anti-AKT, anti-p-AKT specific antibodies. (B) MKN-45 human gastric cancer cells were grown in 0.2% FBS in DMEM for 24 hours. Cells were then exposed for 2 hours to cMP-RM-1 #1, hMP-RM-1 #6, hMP-RM-1 #10 or hMP-RM-1 #20 antibody variants at 10 µg/ml, or MET inhibitor SU11274 at 1 µg/ml. Cells were lysed and analyzed for p-MET, p-ErbB3 and ErbB3 levels by Western blotting with anti-p-MET, anti-p-ErbB3 and anti-ErbB3 specific antibodies. The same filter was re-probed with anti-AKT as a loading control.

Figure 18:
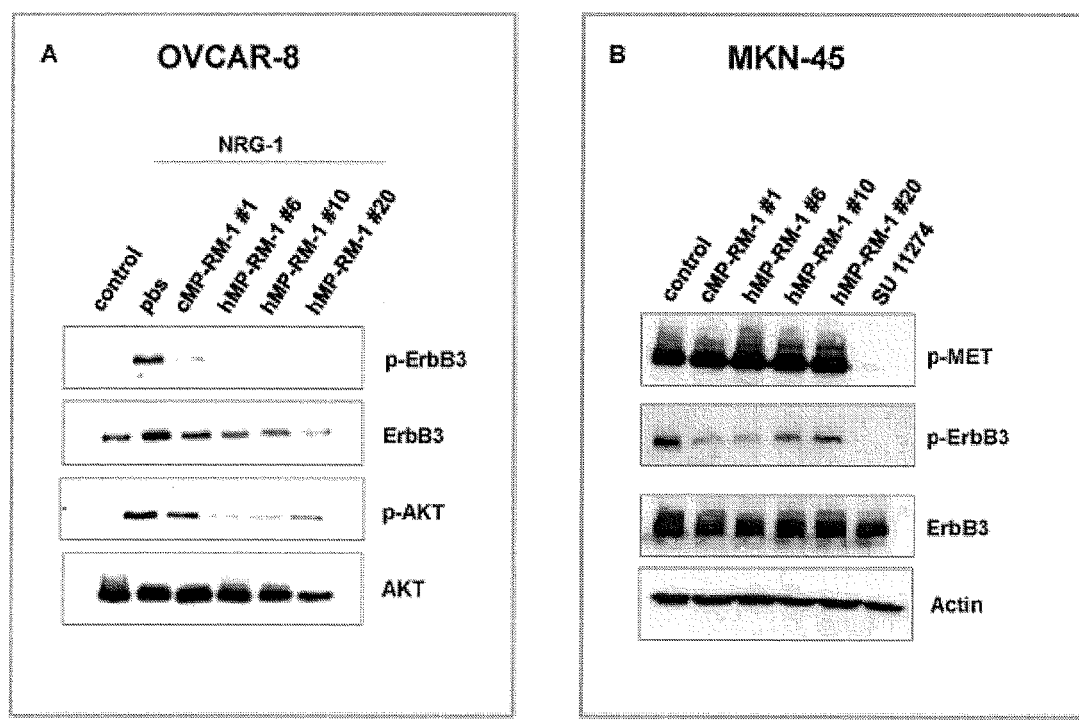
FIG. 18 shows the inhibitory effect of cMP-RM-1 #1, hMP-RM-1 #6, hMP-RM-1 #10 and hMP-RM-1 #20 antibody variants on the phosphorylation of ErbB3 and AKT in human ovarian (A) and gastric (B) cancer cells.

Results:

Treatment of OVCAR-8 human ovarian cancer with the antibody variants inhibits ErbB-3 and AKT ligand-induced phosphorylation and promotes down-regulation of ErbB3 receptor (FIG. 18). MKN-45 cells show a ligand-independent, MET-dependent phosphorylation of ErbB3 receptor. The MP-RM-1 antibody variants are able to inhibit this basal activity (FIG. 18).

Example 21

Chimeric and Humanized MP-RM-1 Antibody Variants Inhibit Colony Formation Ability of Human Melanoma and Gastric Cancer Cells Materials and Methods:

$1.5 \times 10^4$ IR-8 human melanoma or MKN-45 human gastric cancer cells were suspended in 0.3% agarose in RPMI 1640 containing 10% FBS and layered onto a 2 ml bed of 0.5% agarose in six-well plate dishes. Cells were incubated at 37° C. in a humidified atmosphere containing 5% CO2. After agarose solidification, 5-10-20 µg/ml of cMP-RM-1 #1, hMP-RM-1 #6, hMP-RM-1 #10 or hMP-RM-1 #20 antibody variants or PBS were added to dishes. Treatment administration is repeated every alternate day. The number of colonies in 4 different microscope field at 10 magnification was determined by light microscopy after 10-16 days.

Figure 19A:
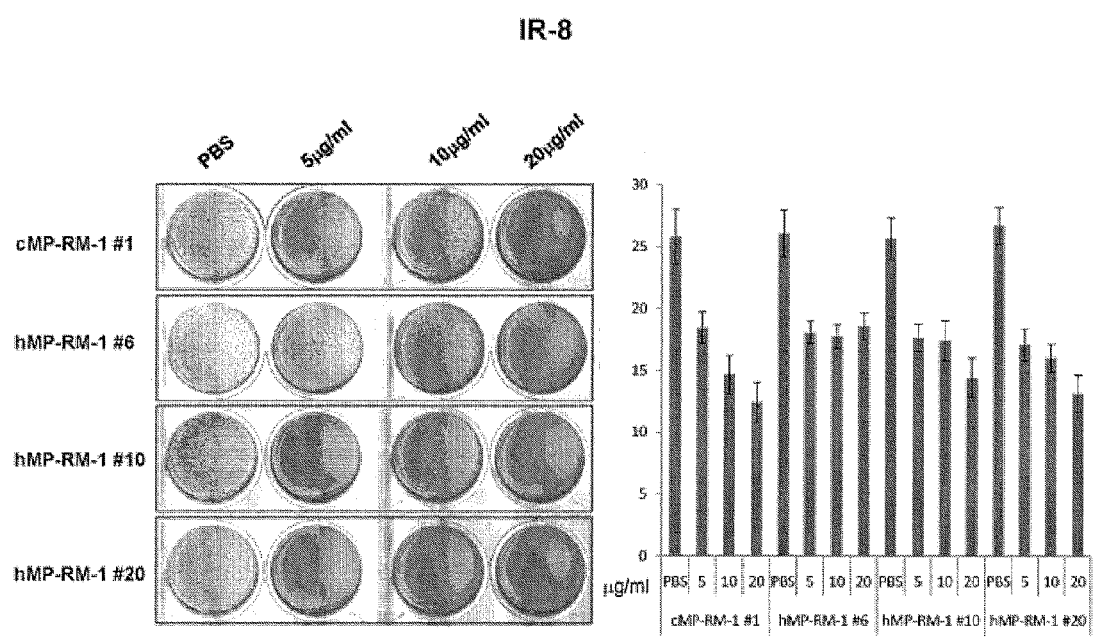
FIG. 19 shows the inhibitory effect of cMP-RM-1 #1, hMP-RM-1 #6, hMP-RM-1 #10 and hMP-RM-1 #20 antibody variants on human melanoma (A) or gastric cancer (B) cell colony formation in soft agar.
Figure 19B:
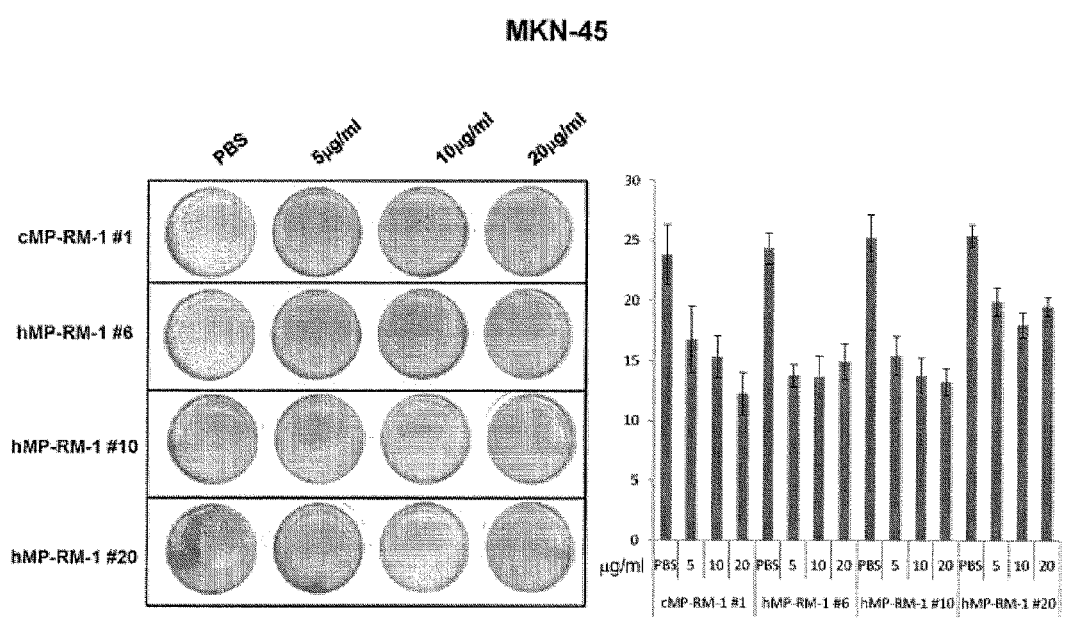

Results:

The indicated MP-RM-1 antibody variants reduce the number and dimensions of IR-8 and MKN-45 colonies in soft agar (FIG. 19A-B). The bar chart represents the number of the colonies in each.

Example 22

Effect of Chimeric and Humanized MP-RM-1 Antibody Variants on Human Ovarian Cancer Xenografts Materials and Methods:

OVCAR-8 human ovarian cancer xenografts were established by injecting subcutaneously $5 \times 10^6$ cells in 7-week old CD1 nude mice. Two days later, mice were randomized into five groups of 10 animals and injected intraperitoneally twice a week for 4 weeks with vehicle (PBS) or 20 mg/kg of cMP-RM-1 #1, hMP-RM-1 #6, hMP-RM-1 #10 or hMP-RM-1 #20 antibody variants. Tumor volume was monitored by a caliper. Error bars indicated SE in each group. The arrows indicate the start (S) and the end (E) of treatment.

Figure 20:
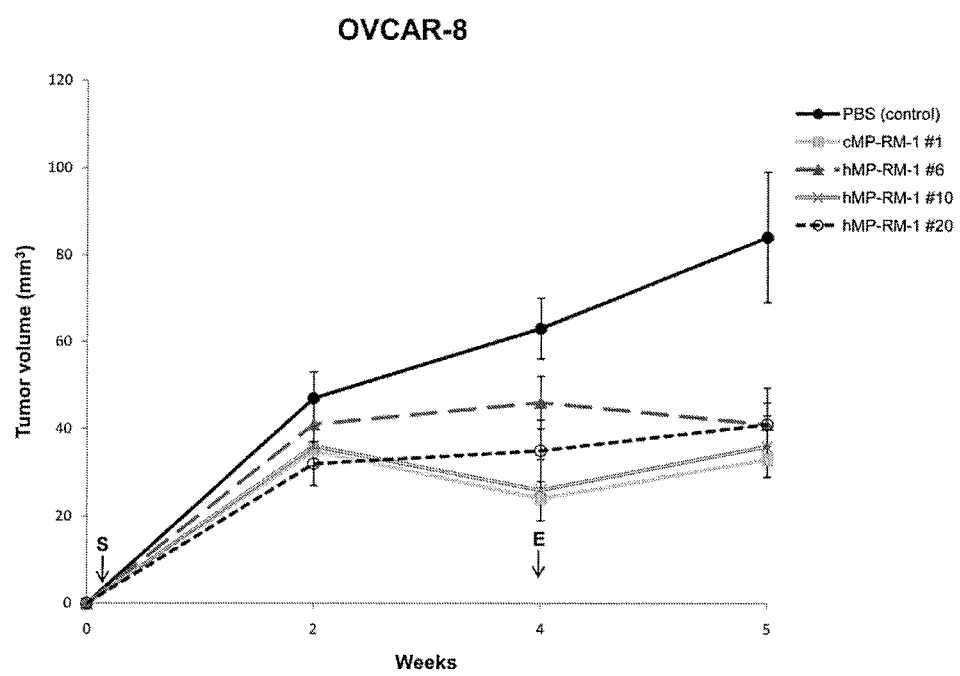
FIG. 20 shows that tumor xenografts of mice treated with cMP-RM-1 #1, hMP-RM-1 #6, hMP-RM-1 #10 and hMP-RM-1 #20 antibody variants grow significantly less than those of control mice.

Results:

Tumor xenografts of mice with chimeric or humanized antibody variants grow significantly slower than those of control mice ($P<0.05$). (FIG. 20).

REFERENCES

1. World Health Statistics, World Health Organization, 2008.
2. A Jemal, R Siegel, E Ward et al. Cancer Statistics, 2009. CA Cancer J Clin 59: 225-49 (2009).
3. Mehlen P, Puisieux A. Metastasis: a question of life or death. Nat Rev Cancer; 6:449-58 (2006).
4. Chambers A F, Groom A C, MacDonald I C. Dissemination and growth of cancer cells in metastatic sites. Nat Rev Cancer 2:563-72 (2002).
5. Gossage L, Eisen T. Targeting multiple kinase pathways: a change in paradigm. Clin Cancer Res. March 9 (2010).
6. N. E. Hynes, MacDonald G. ErbB receptors and signaling pathways in cancer. Curr Opin Cell Biol 21(2):177-84 (2009).
7. T. Holbro, G. Civenni, N. E. Hynes, The ErbB receptors and their role in cancer progression. Exp Cell Res 284, 99-110 (2003).
8. Browne B C, O'Brien N, Duffy et al. HER-2 signaling and inhibition in breast cancer. Curr Cancer Drug Targets 9(3): 419-38 (2009).

9. Harari D, Yarden Y. Molecular mechanisms underlying ErbB2/ERBB2 action in breast cancer. Oncogene 19 (53): 6102-14 (2000).
10. Alimandi M, Wang L M, Bottaro D et al. Epidermal growth factor and betacellulin mediate signal transduction through co-expressed ErbB2 and ErbB3 receptors. EMBO J 16(18): 5608-17 (1997).
11. Alimandi M, Romano A, Curia M C, Muraro R et al. Cooperative signaling of ErbB3 and ErbB2 in neoplastic transformation and human mammary carcinomas. Oncogene 10(9): 1813-21 (1995).
12. N. E. Hynes, Targeting ERBB receptors in cancer. Recent Results Cancer Res. 172, 45-57 (2007).
13. N. E. Hynes, H. A. Lane, ERBB receptors and cancer: the complexity of targeted inhibitors. Nat Rev Cancer 5, 341-54 (2005).
14. J. Baselga and S. M. Swain, Novel anticancer targets: revisiting ERBB2 and discovering ERBB3. Nat. Rev. Cancer. 9, 463-75, (2009).
15. B. Tanner, D Hasenclever, K Stern et al. ErbB3 predicts survival in Ovarian cancer. J. Clin. Onco. 24, 17-23 (2006).
16. M. Reschke, D. Mihic-Probst, E. H. van der Horst et al. ERBB3 is a determinant for poor prognosis in Melanoma. Clin. Canc. Res. 14, 5188-97 (2008).
17. M. Soler, F Manicni, O. Meca-Cortes et al. ERBB3 is required for the maintenance of neuregulin-dependent and -independent attributes of malignant progression in prostate cancer cells. Int. J. Cancer 125, 2565-75 (2009).
18. D. F. Stern, ERBB3/ERBB3 and ERBB2/ERBB2 duet in mammary development and breast cancer. J Mammary Gland Biol Neoplasia. 13, 215-23 (2008).
19. J. A. Engelman, K. Zejnullahu, T Mitsudomi et al. MET amplification leads to Gefitinib resistance in lung cancer by activating ERBB3 signalling. Science 316, 1039-43 (2007).
20. L. M. Weiner, M. V. Dhodapkar and S. Ferrone. Monoclonal antibodies for cancer immunotherapy. Lancet 373, 1033-1040 (2009).
21. X. Huang, L. Gao, S. Wang et al. Heterotrimerization of the growth factor receptors ErbB2. ErbB3, and Insulin-like growth factor-1 receptor in breast cancer cells resistant to Herceptin. Canc. Res. 70, 1204-14 (2010).
22. T. Holbro, R. Beerli, F. Maurer et al. The ErbB2/ErbB3 heterodimer functions a san oncogenic unit: ErbB2 requires ErbB3 to drive breast tumor cell proliferation. PNAS 100, 8933-8938 (2003).
23. Y Yarden. The EGFR family and its ligands in human cancer: signaling mechanisms and therapeutic opportunities. EUR. J. Cancer 37, 3-8 (2001).
24. M. R. Freeman. HER-2/ERBB3 heterodimers in prostate cancer: whither HER1/EGFR ? Cancer Cell 6:427-428 (2004).
25. Kohler G, Milstein C. Continuous cultures of fused cells secreting antibody of predefined specificity. Nature 1975; 256:495-497.
26. Clackson T, Hoogenboom H R, Griffiths A D, Winter G. Making antibody fragments using phage display libraries. Nature 1991; 15; 352(6336):624-8.
27. Jones et al., Replacing the complementarity-determining regions in a human antibody with those from a mouse, Nature, 321:522-525 (1986).
28. Riechmann et al., Reshaping human antibodies for therapy, Nature, 332:323-327 (1988).
29. Verhoeyen et al., Reshaping human antibodies: grafting an antilysozome activity, Science, 239:1534-1536 (1988).

The invention claimed is:

1. An antibody or fragment thereof which binds to the ErbB3 receptor and which comprises:
   (a) a heavy chain amino acid sequence encoded by SEQ ID NO: 1 or at least the variable domain thereof or an amino acid sequence having a sequence identity of at least 95% thereto, wherein the heavy chain amino acid sequence comprises complementarity determining regions CDR1, CDR2, and CDR3, wherein CDR1 comprises the amino acid residues 50-54 from SEQ ID NO:3, CDR2 comprises the amino acid residues 69-85 from SEQ ID NO:3, and CDR3 comprises the amino acid residues 118-130 from SEQ ID NO:3 and
   (b) a light chain amino acid sequence encoded by SEQ ID NO: 2 or at least the variable domain thereof or an amino acid sequence having a sequence identity of at least 95% thereto, wherein the light chain amino acid sequence comprises complementarity determining regions CDR1, CDR2, and CDR3, wherein CDR1 comprises the amino acid residues 46-60 from SEQ ID NO:13, CDR2 comprises the amino acid residues 76-82 from SEQ ID NO:13 and CDR3 comprises the amino acid residues 115-123 from SEQ ID NO:13.

2. The antibody according to claim 1, wherein binding of said antibody to ErbB3 reduces ErbB3 mediated signal transduction.

3. The antibody of claim 2, wherein said reduction of signal transduction is caused by a down-regulation of ErbB3.

4. The antibody according to claim 2, having the ability to decrease levels of ErbB3 on cell surfaces.

5. The antibody of claim 1, which is a polyclonal antibody or a monoclonal antibody, a humanized antibody, a chimeric antibody, a multispecific antibody, or a fragment thereof that binds to the ErbB3 receptor.

6. The antibody of claim 5, wherein the multispecific antibody is a bispecific antibody and the monoclonal antibody is a recombinant antibody.

7. The antibody according to claim 1, which is a Fab fragment, a Fab' fragment, a F(ab') fragment, a Fv-fragment, a diabody, ScFv, SMIP, single chain antibody, affibody, avimer, nanobody or a single domain antibody.

8. The antibody according to claim 1, wherein the antibody isotype is selected from the group consisting of an IgG1, an IgG2, an IgG3, an IgG4, an IgM, an IgA1, an IgA2, an IgAsec, an IgD, and an IgE antibody.

9. The antibody according to claim 1, produced from the hybridoma cell line DSM ACC3018 deposited at the Deutsche Sammlung von Mikroorganismen and Zellkulturen (DSMZ).

10. The antibody according to claim 1, comprising at least one sequence as shown in SEQ ID NOs. 3-15.

11. The antibody according to claim 10, comprising at least one sequence as shown in SEQ ID NOs. 8-15.

12. An antibody according to Table 1 which is selected from the group consisting of cMP-RM-1 #1, cMP-RM-1 #2, cMP-RM-1 #3, cMP-RM-1 #4, hMP-RM-1 #5, hMP-RM-1 #6, hMP-RM-1 #7, hMP-RM-1 #8, hMP-RM-1 #9, hMP-RM-1 #10, hMP-RM-1 #11, hMP-RM-1 #12, hMP-RM-1 #13, hMP-RM-1 #14, hMP-RM-1 #15, hMP-RM-1 #16, hMP-RM-1 #17, hMP-RM-1 #18, hMP-RM-1 #19, and hMP-RM-1 #20 (c, chimeric antibody; h, humanized antibody).

13. The antibody according to claim 1, which is coupled to a labelling group.

14. The antibody according to claim 1, which is coupled to an effector group.

15. A nucleic acid encoding an antibody or antibody fragment according to claim 1.

16. A vector comprising a nucleic acid according to claim 15.

17. The vector of claim 16, which is an expression vector and the nucleic acid sequence is operably linked to a control sequence.

18. An isolated host cell comprising the nucleic acid of claim 15.

19. An isolated host cell comprising the vector of claim 16.

20. An isolated host cell comprising the vector of claim 17.

21. A pharmaceutical composition comprising an antibody according to claim 1 and a pharmaceutically acceptable carrier, diluent and/or excipient.

22. The composition according to claim 21, wherein the composition is effective for treating hyperproliferative diseases.

23. The composition of claim 22, wherein the hyperproliferative disease is melanoma, breast cancer, ovarian cancer, gastrointestinal/colon cancer, lung cancer or prostate cancer.

24. The composition according to claim 21, comprising a further active agent.

25. The composition of claim 24, wherein the further active agent is an anti-neoplastic agent selected from the group consisting of antibodies, antibody fragments, small molecules, antimetabolites, alkylating agents, topoisomerase inhibitors, microtubule-targeting agents, kinase inhibitors, protein synthesis inhibitors, immuno-therapeutics, hormones or analogs thereof, and mTOR inhibitors.

26. The composition of claim 21, wherein the composition is in a form suitable to be administered intravenously, intramuscularly, and/or subcutaneously.

27. A method of inhibiting EGF-like ligand mediated phosphorylation of ErbB3 in a subject, comprising administering to the subject an antibody or antigen binding portion thereof of claim 1, in an amount sufficient to inhibit EGF-like mediated phosphorylation of ErbB3.

28. The method of claim 27, wherein the subject is human.

29. A process of manufacturing an antibody that binds to an ErbB3 receptor comprising the step of purifying the antibody expressed from an isolated host cell comprising an expression vector comprising a nucleic acid encoding an antibody or antibody fragment according to claim 1, wherein the nucleic acid sequence is operably linked to a control sequence.

30. A method of treating a hyperproliferative disease caused by ErbB3 expression in a patient in need thereof, comprising administering to said patient an effective amount of an antibody according to claim 1.

31. The method of claim 30, wherein the hyperproliferative disease is a neoplastic disease or cancer.

32. The method of claim 31, wherein the hyperproliferative disease is melanoma, breast cancer, ovarian cancer, gastrointestinal/colon cancer, lung cancer or prostate cancer.

33. The method of claim 30, wherein the antibody is administered in combination with a further therapeutic composition and/or irradiation.

34. The antibody according to claim 1, wherein the antibody or fragment thereof comprises:

(a) a heavy chain amino acid sequence encoded by sequence SEQ ID NO: 1 or an amino acid sequence selected from the group consisting of SEQ ID NO: 3, SEQ ID NO: 4, SEQ ID NO: 5, SEQ ID NO: 8, SEQ ID NO: 9, SEQ ID NO: 10, and SEQ ID NO: 11 and (b) a light chain amino acid sequence encoded by sequence SEQ ID NO: 2 or an amino acid sequence selected from the group consisting of SEQ ID NO: 6, SEQ ID NO: 7, SEQ ID NO: 12, SEQ ID NO: 13, SEQ ID NO: 14, and SEQ ID NO: 15.

* * * * *

SEQUENCE LISTING

<160> NUMBER OF SEQ ID NOS: 15

<210> SEQ ID NO 1
<211> LENGTH: 363
<212> TYPE: DNA
<213> ORGANISM: Artificial Sequence
<220> FEATURE:
<223> OTHER INFORMATION: VH sequence

<400> SEQUENCE: 1

```
gacgtgcagc tggtggagtc tggggagac ttagtgaagc ctggagggtc cctgaaactc      60
tcctgtgtag tctctggatt cactttcagt acctatggca tgtcttgggt tcgccagact    120
ccagacagga ggctggagtg ggtcgcaacc attagtcatg gtgacggtta tacctactat    180
ccagacagtg tgaaggggcg attcaccatc tccagagaca atgccaagaa caccctgcac    240
ctgcaaatga gcagtctgaa gtctgaggac acagccatgt attactgtgc aagacatggg    300
gattacgacg atgattacta tgctatggac tactggggtc aaggaacctc agtcaccgtc    360
tca                                                                  363
```

<210> SEQ ID NO 2
<211> LENGTH: 343
<212> TYPE: DNA
<213> ORGANISM: Artificial Sequence
<220> FEATURE:
<223> OTHER INFORMATION: VL sequence

<400> SEQUENCE: 2

```
gatattgtga tgacccagtc tccatcctcc ctgactgtga tagcaggaga gaaggtcact      60
```

-continued

```
atgagctgca agtccagtca gagtctgtta aacagtggaa atcaaaagaa ctacttgacc    120
tggtaccaac agaaaccagg gcagcctcct aaactgttga tctactgggc atccactagg    180
gaatctgggg tccctgatcg cttcacaggc agtggatctg gaacagattt cactctcacc    240
atcagcagtg tgcaggctga agacctggca gtttattact gtcagaatga atatacttat    300
ccgctcacgt tcggtgctgg gaccaagctg gagctgaaac ggg                     343
```

<210> SEQ ID NO 3
<211> LENGTH: 471
<212> TYPE: PRT
<213> ORGANISM: Artificial Sequence
<220> FEATURE:
<223> OTHER INFORMATION: CHIMERIC IgG1 HC SEQUENCE

<400> SEQUENCE: 3

```
Met Asn Phe Gly Leu Arg Leu Ile Phe Leu Val Leu Thr Leu Lys Gly
1               5                   10                  15

Val Gln Cys Asp Val Gln Leu Val Glu Ser Gly Gly Asp Leu Val Lys
            20                  25                  30

Pro Gly Gly Ser Leu Lys Leu Ser Cys Val Val Ser Gly Phe Thr Phe
        35                  40                  45

Ser Thr Tyr Gly Met Ser Trp Val Arg Gln Thr Pro Asp Arg Arg Leu
    50                  55                  60

Glu Trp Val Ala Thr Ile Ser His Gly Asp Gly Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu His Leu Gln Met Ser Ser Leu Lys Ser Glu Asp Thr Ala Met
            100                 105                 110

Tyr Tyr Cys Ala Arg His Gly Asp Tyr Asp Asp Asp Tyr Tyr Ala Met
        115                 120                 125

Asp Tyr Trp Gly Gln Gly Thr Ser Val Thr Phe Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
```

```
                305                 310                 315                 320
Asn Ser Thr Tyr Arg Val Val Ser Val Leu Thr Val Leu His Gln Asp
                    325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 4
<211> LENGTH: 467
<212> TYPE: PRT
<213> ORGANISM: Artificial Sequence
<220> FEATURE:
<223> OTHER INFORMATION: CHIMERIC IgG2 HC SEQUENCE

<400> SEQUENCE: 4

Met Asn Phe Gly Leu Arg Leu Ile Phe Leu Val Leu Thr Leu Lys Gly
1               5                   10                  15
Val Gln Cys Asp Val Gln Leu Val Glu Ser Gly Gly Asp Leu Val Lys
                20                  25                  30
Pro Gly Gly Ser Leu Lys Leu Ser Cys Val Val Ser Gly Phe Thr Phe
            35                  40                  45
Ser Thr Tyr Gly Met Ser Trp Val Arg Gln Thr Pro Asp Arg Arg Leu
        50                  55                  60
Glu Trp Val Ala Thr Ile Ser His Gly Asp Gly Tyr Thr Tyr Tyr Pro
65                  70                  75                  80
Asp Ser Val Lys Gly Arg Phe Thr Ile Ser Arg Asp Asn Ala Lys Asn
                85                  90                  95
Thr Leu His Leu Gln Met Ser Ser Leu Lys Ser Glu Asp Thr Ala Met
            100                 105                 110
Tyr Tyr Cys Ala Arg His Gly Asp Tyr Asp Asp Tyr Tyr Ala Met
        115                 120                 125
Asp Tyr Trp Gly Gln Gly Thr Ser Val Thr Phe Ser Ser Ala Ser Thr
    130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
```

```
            195                 200                 205
Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Met Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ser Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 5
<211> LENGTH: 503
<212> TYPE: PRT
<213> ORGANISM: Artificial Sequence
<220> FEATURE:
<223> OTHER INFORMATION: CHIMERIC IgG3 HC SEQUENCE

<400> SEQUENCE: 5

Met Asn Phe Gly Leu Arg Leu Ile Phe Leu Val Leu Thr Leu Lys Gly
1               5                   10                  15

Val Gln Cys Asp Val Gln Leu Val Glu Ser Gly Gly Asp Leu Val Lys
            20                  25                  30

Pro Gly Gly Ser Leu Lys Leu Ser Cys Val Val Ser Gly Phe Thr Phe
        35                  40                  45

Ser Thr Tyr Gly Met Ser Trp Val Arg Gln Thr Pro Asp Arg Arg Leu
    50                  55                  60

Glu Trp Val Ala Thr Ile Ser His Gly Asp Gly Tyr Thr Tyr Tyr Pro
65                  70                  75                  80

Asp Ser Val Lys Gly Arg Phe Thr Ile Ser Arg Asp Asn Ala Lys Asn
```

```
            85                  90                  95
Thr Leu His Leu Gln Met Ser Ser Leu Lys Ser Glu Asp Thr Ala Met
            100                 105                 110
Tyr Tyr Cys Ala Arg His Gly Asp Tyr Asp Asp Tyr Tyr Ala Met
            115                 120                 125
Asp Tyr Trp Gly Gln Gly Thr Ser Val Thr Phe Ser Ser Ala Ser Thr
            130                 135                 140
Lys Gly Pro Ser Val Phe Pro Leu Ala Pro Cys Ser Arg Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Thr Cys
            210                 215                 220
Asn Val Asn His Lys Pro Ser Asn Thr Lys Val Asp Lys Arg Val Glu
225                 230                 235                 240
Leu Lys Thr Pro Leu Gly Asp Thr Thr His Thr Cys Pro Arg Cys Pro
                245                 250                 255
Glu Pro Lys Ser Cys Asp Thr Pro Pro Pro Cys Pro Arg Cys Pro Glu
            260                 265                 270
Pro Lys Ser Cys Asp Thr Pro Pro Pro Cys Pro Arg Cys Pro Ala Pro
            275                 280                 285
Glu Leu Leu Gly Gly Pro Ser Val Phe Leu Phe Pro Pro Lys Pro Lys
290                 295                 300
Asp Thr Leu Met Ile Ser Arg Thr Pro Glu Val Thr Cys Val Val Val
305                 310                 315                 320
Asp Val Ser His Glu Asp Pro Glu Val Gln Phe Lys Trp Tyr Val Asp
                325                 330                 335
Gly Val Glu Val His Asn Ala Lys Thr Lys Pro Arg Glu Glu Gln Tyr
            340                 345                 350
Asn Ser Thr Phe Arg Val Val Ser Val Leu Thr Val Leu His Gln Asp
            355                 360                 365
Trp Leu Asn Gly Lys Glu Tyr Lys Cys Lys Val Ser Asn Lys Ala Leu
            370                 375                 380
Pro Ala Pro Ile Glu Lys Thr Ile Ser Lys Thr Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Thr Cys Leu Val Lys Gly Phe Tyr Pro Ser Asp
            420                 425                 430
Ile Ala Val Glu Trp Glu Ser Ser Gly Gln Pro Glu Asn Asn Tyr Asn
            435                 440                 445
Thr Thr Pro Pro Met Leu Asp Ser Asp Gly Ser Phe Phe Leu Tyr Ser
            450                 455                 460
Lys Leu Thr Val Asp Lys Ser Arg Trp Gln Gln Gly Asn Ile Phe Ser
465                 470                 475                 480
Cys Ser Val Met His Glu Ala Leu His Asn Arg Phe Thr Gln Lys Ser
                485                 490                 495
Leu Ser Leu Ser Pro Gly Lys
            500
```

<210> SEQ ID NO 6
<211> LENGTH: 240
<212> TYPE: PRT
<213> ORGANISM: Artificial Sequence
<220> FEATURE:
<223> OTHER INFORMATION: CHIMERIC LC KAPPA SEQUENCE

<400> SEQUENCE: 6

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Ile Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Glu Tyr Thr Tyr Pro Leu Thr Phe Gly Ala Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 7
<211> LENGTH: 239
<212> TYPE: PRT
<213> ORGANISM: Artificial Sequence
<220> FEATURE:
<223> OTHER INFORMATION: CHIMERIC LC LAMBDA SEQUENCE

<400> SEQUENCE: 7

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Ile Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg

```
65                  70                  75                  80
Glu Ser Gly Val Pro Asp Arg Phe Thr Gly Ser Gly Ser Gly Thr Asp
                85                  90                  95
Phe Thr Leu Thr Ile Ser Ser Val Gln Ala Glu Asp Leu Ala Val Tyr
               100                 105                 110
Tyr Cys Gln Asn Glu Tyr Thr Tyr Pro Leu Thr Phe Gly Ala Gly Thr
               115                 120                 125
Lys Leu Thr Val Leu Gly Gln Pro Lys Ala Ala Pro Ser Val Thr Leu
               130                 135                 140
Phe Pro Pro Ser Ser Glu Glu Leu Gln Ala Asn Lys Ala Thr Leu Val
145                 150                 155                 160
Cys Leu Ile Ser Asp Phe Tyr Pro Gly Ala Val Thr Val Ala Trp Lys
               165                 170                 175
Ala Asp Ser Ser Pro Val Lys Ala Gly Val Glu Thr Thr Thr Pro Ser
               180                 185                 190
Lys Gln Ser Asn Asn Lys Tyr Ala Ala Ser Ser Tyr Leu Ser Leu Thr
               195                 200                 205
Pro Glu Gln Trp Lys Ser His Arg Ser Tyr Ser Cys Gln Val Thr His
               210                 215                 220
Glu Gly Ser Thr Val Glu Lys Thr Val Ala Pro Thr Glu Cys Ser
225                 230                 235

<210> SEQ ID NO 8
<211> LENGTH: 471
<212> TYPE: PRT
<213> ORGANISM: Artificial Sequence
<220> FEATURE:
<223> OTHER INFORMATION: HUMANIZED IgG1 HC SEQUENCE 1

<400> SEQUENCE: 8

Met Asn Phe Gly Leu Arg Leu Ile Phe Leu Val Leu Thr Leu Lys Gly
1               5                   10                  15
Val Gln Cys Asp Val Gln Leu Val Glu Ser Gly Gly Gly Leu Val Gln
                20                  25                  30
Pro Gly Gly Ser Leu Arg Leu Ser Cys Ala Ala Ser Gly Phe Thr Phe
            35                  40                  45
Ser Thr Tyr Gly Met Ser Trp Val Arg Gln Thr Pro Asp Lys Arg Leu
        50                  55                  60
Glu Trp Val Ala Thr Ile Ser His Gly Asp Gly Tyr Thr Tyr Tyr Pro
65                  70                  75                  80
Asp Ser Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Met
               100                 105                 110
Tyr Tyr Cys Ala Arg His Gly Asp Tyr Asp Asp Tyr Tyr Ala Met Asp
               115                 120                 125
Tyr Trp Gly Gln Gly Thr Leu Val Thr Val Ser Ser Ala Ser Thr Lys
           130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
               165                 170                 175
Val Thr Val Ser Trp Asn Ser Gly Ala Leu Thr Ser Gly Val His Thr
              180                 185                 190
Phe Pro Ala Val Leu Gln Ser Ser Gly Leu Tyr Ser Leu Ser Ser
```

```
            195                 200                 205
Val Val Thr Val Pro Ser Ser Leu Gly Thr Gln Thr Tyr Ile Cys
    210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
        450                 455                 460
Leu Ser Leu Ser Pro Gly Lys
465                 470

<210> SEQ ID NO 9
<211> LENGTH: 471
<212> TYPE: PRT
<213> ORGANISM: Artificial Sequence
<220> FEATURE:
<223> OTHER INFORMATION: HUMANIZED IgG1 HC SEQUENCE 2

<400> SEQUENCE: 9

Met Asn Phe Gly Leu Arg Leu Ile Phe Leu Val Leu Thr Leu Lys Gly
1               5                   10                  15
Val Gln Cys Asp Val Gln Leu Val Glu Ser Gly Gly Gly Leu Val Gln
            20                  25                  30
Pro Gly Gly Ser Leu Arg Leu Ser Cys Ala Val Ser Gly Phe Thr Phe
        35                  40                  45
Ser Thr Tyr Gly Met Ser Trp Val Arg Gln Ala Pro Gly Lys Gly Leu
    50                  55                  60
Glu Trp Val Ala Thr Ile Ser His Gly Asp Gly Tyr Thr Tyr Tyr Pro
65                  70                  75                  80
Asp Ser Val Lys Gly Arg Phe Thr Ile Ser Arg Asp Asn Ser Lys Asn
```

```
                    85                  90                  95
Thr Leu Tyr Leu Gln Met Asn Ser Leu Arg Ala Glu Asp Thr Ala Val
                100                 105                 110
Tyr Tyr Cys Ala Arg His Gly Asp Tyr Asp Asp Tyr Tyr Ala Met
            115                 120                 125
Asp Tyr Trp Gly Gln Gly Thr Leu Val Thr Val Ser Ser Ala Ser Thr
        130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
        210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
        450                 455                 460
Leu Ser Leu Ser Pro Gly Lys
465                 470

<210> SEQ ID NO 10
<211> LENGTH: 471
<212> TYPE: PRT
<213> ORGANISM: Artificial Sequence
```

<220> FEATURE:
<223> OTHER INFORMATION: HUMANIZED IgG1 HC SEQUENCE 3

<400> SEQUENCE: 10

```
Met Asn Phe Gly Leu Arg Leu Ile Phe Leu Val Leu Thr Leu Lys Gly
1               5                   10                  15

Val Gln Cys Asp Val Gln Leu Val Glu Ser Gly Gly Asp Leu Val Lys
            20                  25                  30

Pro Gly Gly Ser Leu Lys Leu Ser Cys Val Ala Ser Gly Phe Thr Phe
        35                  40                  45

Ser Thr Tyr Gly Met Ser Trp Val Arg Gln Thr Pro Asp Lys Arg Leu
    50                  55                  60

Glu Trp Val Ala Thr Ile Ser His Gly Asp Gly Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Gly Asp Tyr Asp Asp Tyr Tyr Ala Met
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400
```

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465             470

<210> SEQ ID NO 11
<211> LENGTH: 471
<212> TYPE: PRT
<213> ORGANISM: Artificial Sequence
<220> FEATURE:
<223> OTHER INFORMATION: HUMANIZED IgG1 HC SEQUENCE 4

<400> SEQUENCE: 11

Met Asn Phe Gly Leu Arg Leu Ile Phe Leu Val Leu Thr Leu Lys Gly
1               5                   10                  15

Val Gln Cys Asp Val Gln Leu Val Glu Ser Gly Gly Asp Leu Val Lys
            20                  25                  30

Pro Gly Gly Ser Leu Lys Leu Ser Cys Val Ala Ser Gly Phe Thr Phe
            35                  40                  45

Ser Thr Tyr Gly Met Ser Trp Val Arg Gln Thr Pro Asp Arg Arg Leu
        50                  55                  60

Glu Trp Val Ala Thr Ile Ser His Gly Asp Gly Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu His Leu Gln Met Ser Ser Leu Lys Ser Glu Asp Thr Ala Met
            100                 105                 110

Tyr Tyr Cys Ala Arg His Gly Asp Tyr Asp Asp Tyr Tyr Ala Met
            115                 120                 125

Asp Tyr Trp Gly Gln Gly Thr Thr Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

-continued

```
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
450                 455                 460
Leu Ser Leu Ser Pro Gly Lys
465                 470

<210> SEQ ID NO 12
<211> LENGTH: 240
<212> TYPE: PRT
<213> ORGANISM: Artificial Sequence
<220> FEATURE:
<223> OTHER INFORMATION: HUMANIZED LC KAPPA SEQUENCE 1

<400> SEQUENCE: 12

Met Glu Ser Gln Thr Gln Val Leu Ile Ser Leu Leu Phe Trp Val Ser
1               5                   10                  15
Gly Thr Cys Gly Asp Ile Val Met Thr Gln Ser Pro Asp Ser Leu Ala
            20                  25                  30
Val Ser Leu Gly Glu Arg Ala Thr Ile Asn Cys Lys Ser Ser Gln Ser
        35                  40                  45
Leu Leu Asn Ser Gly Asn Gln Lys Asn Tyr Leu Thr Trp Tyr Gln Gln
    50                  55                  60
Lys Pro Gly Gln Pro Pro Lys Leu Leu Ile Tyr Trp Ala Ser Thr Arg
65                  70                  75                  80
Glu Ser Gly Val Pro Asp Arg Phe Ser Gly Ser Gly Ser Gly Thr Asp
                85                  90                  95
Phe Thr Leu Thr Ile Ser Ser Leu Gln Ala Glu Asp Val Ala Val Tyr
            100                 105                 110
Tyr Cys Gln Asn Glu Tyr Thr Tyr Pro Leu Thr Phe Gly Gly Gly Thr
        115                 120                 125
Lys Leu Glu Ile Lys Arg Thr Val Ala Ala Pro Ser Val Phe Ile Phe
    130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
```

```
Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240
```

<210> SEQ ID NO 13
<211> LENGTH: 240
<212> TYPE: PRT
<213> ORGANISM: Artificial Sequence
<220> FEATURE:
<223> OTHER INFORMATION: HUMANIZED LC KAPPA SEQUENCE 2

<400> SEQUENCE: 13

```
Met Glu Ser Gln Thr Gln Val Leu Ile Ser Leu Leu Phe Trp Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
            35                  40                  45

Leu Leu Asn Ser Gly Asn Gln Lys Asn Tyr Leu Thr Trp Tyr Gln Gln
50                  55                  60

Lys Pro Gly Lys Ala Pro Lys Leu Leu Ile Tyr Trp Ala Ser Thr Arg
65                  70                  75                  80

Glu Ser Gly Val Pro Ser Arg Phe Ser Gly Ser Gly Ser Gly Thr Asp
            85                  90                  95

Phe Thr Leu Thr Ile Ser Ser Leu Gln Pro Glu Asp Phe Ala Thr Tyr
            100                 105                 110

Tyr Cys Gln Asn Glu Tyr Thr Tyr Pro Leu Thr Phe Gly Gln Gly Thr
            115                 120                 125

Lys Val Glu Ile Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240
```

<210> SEQ ID NO 14
<211> LENGTH: 240
<212> TYPE: PRT
<213> ORGANISM: Artificial Sequence
<220> FEATURE:
<223> OTHER INFORMATION: HUMANIZED LC KAPPA SEQUENCE 3

<400> SEQUENCE: 14

```
Met Glu Ser Gln Thr Gln Val Leu Ile Ser Leu Leu Phe Trp Val Ser
```

```
                1               5                   10                  15
            Gly Thr Cys Gly Asp Ile Val Met Thr Gln Ser Pro Asp Ser Leu Thr
                        20                  25                  30

Val Ser Leu Gly Glu Arg Ala Thr Ile Asn Cys Lys Ser Ser Gln Ser
                        35                  40                  45

Leu Leu Asn Ser Gly Asn Gln Lys Asn Tyr Leu Thr Trp Tyr Gln Gln
                50                      55                  60

Lys Pro Gly Gln Pro Pro Lys Leu Leu Ile Tyr Trp Ala Ser Thr Arg
             65                     70                  75                  80

Glu Ser Gly Val Pro Asp Arg Phe Ser Gly Ser Gly Ser Gly Thr Asp
                            85                  90                  95

Phe Thr Leu Thr Ile Ser Ser Val Gln Ala Glu Asp Val Ala Val Tyr
                            100                 105                 110

Tyr Cys Gln Asn Glu Tyr Thr Tyr Pro Leu Thr Phe Gly Gly Gly Thr
                            115                 120                 125

Lys Leu Glu Leu Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
            145                 150                 155                 160

Leu Leu Asn Asn Phe Tyr Pro Arg Glu Ala Lys Val Gln Trp Lys Val
                            165                 170                 175

Asp Asn Ala Leu Gln Ser Gly Asn Ser Gln Glu Ser Val Thr Glu Gln
                        180                 185                 190

Asp Ser Lys Asp Ser Thr Tyr Ser Leu Ser Ser Thr Leu Thr Leu Ser
                        195                 200                 205

Lys Ala Asp Tyr Glu Lys His Lys Val Tyr Ala Cys Glu Val Thr His
                        210                 215                 220

Gln Gly Leu Ser Ser Pro Val Thr Lys Ser Phe Asn Arg Gly Glu Cys
            225                 230                 235                 240

<210> SEQ ID NO 15
<211> LENGTH: 240
<212> TYPE: PRT
<213> ORGANISM: Artificial Sequence
<220> FEATURE:
<223> OTHER INFORMATION: HUMANIZED LC KAPPA SEQUENCE 4

<400> SEQUENCE: 15

Met Glu Ser Gln Thr Gln Val Leu Ile Ser Leu Leu Phe Trp Val Ser
            1               5                   10                  15

Gly Thr Cys Gly Asp Ile Val Met Thr Gln Ser Pro Ser Ser Leu Thr
                        20                  25                  30

Val Ser Leu Gly Glu Arg Ala Thr Met Ser Cys Lys Ser Ser Gln Ser
                        35                  40                  45

Leu Leu Asn Ser Gly Asn Gln Lys Asn Tyr Leu Thr Trp Tyr Gln Gln
                50                      55                  60

Lys Pro Gly Gln Pro Pro Lys Leu Leu Ile Tyr Trp Ala Ser Thr Arg
             65                     70                  75                  80

Glu Ser Gly Val Pro Asp Arg Phe Ser Gly Ser Gly Ser Gly Thr Asp
                            85                  90                  95

Phe Thr Leu Thr Ile Ser Ser Val Gln Ala Glu Asp Val Ala Val Tyr
                            100                 105                 110

Tyr Cys Gln Asn Glu Tyr Thr Tyr Pro Leu Thr Phe Gly Gly Gly Thr
                            115                 120                 125

Lys Leu Glu Leu Lys Arg Thr Val Ala Ala Pro Ser Val Phe Ile Phe
```

```
            130                 135                 140
Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240
```